(12) United States Patent
Ferguson et al.

(10) Patent No.: US 7,004,927 B2
(45) Date of Patent: Feb. 28, 2006

(54) SAFETY SHIELD FOR MEDICAL NEEDLES

(75) Inventors: F. Mark Ferguson, Salt Lake City, UT (US); B. Chance Bagley, Roy, UT (US); Jeremy W. Snow, North Salt Lake, UT (US)

(73) Assignee: Specialized Health Products, Inc., Bountiful, UT (US)

( * ) Notice: Subject to any disclaimer, the term of this patent is extended or adjusted under 35 U.S.C. 154(b) by 278 days.

(21) Appl. No.: 10/322,288

(22) Filed: Dec. 17, 2002

(65) Prior Publication Data

US 2003/0100868 A1 May 29, 2003

Related U.S. Application Data

(63) Continuation-in-part of application No. 10/202,201, filed on Jul. 23, 2002, which is a continuation-in-part of application No. 09/809,357, filed on Mar. 15, 2001, now Pat. No. 6,595,955.

(60) Provisional application No. 60/424,655, filed on Nov. 7, 2002.

(51) Int. Cl.
*A61M 5/00* (2006.01)

(52) U.S. Cl. .................. 604/110; 604/198; 128/919
(58) Field of Classification Search ............. 604/110, 604/162, 171, 163, 174, 180, 192, 197, 198, 604/263, 164.04, 164.08, 164.01, 170.01, 604/170.02; 128/919
See application file for complete search history.

(56) References Cited

U.S. PATENT DOCUMENTS

| 1,436,707 | A | 11/1922 | Gaschke |
| 4,332,323 | A | 6/1982 | Reenstierna ................. 206/365 |
| 4,373,526 | A | 2/1983 | Kling ......................... 128/215 |
| 4,762,516 | A | 8/1988 | Luther ........................ 605/164 |
| 4,790,828 | A | 12/1988 | Dombrowski ................ 604/198 |
| 4,804,371 | A | 2/1989 | Vaillancourt ................. 604/198 |
| 4,826,490 | A | 5/1989 | Byrne ......................... 604/198 |
| 4,832,696 | A | 5/1989 | Luther ........................ 604/164 |
| 4,834,718 | A | 5/1989 | McDonald .................. 604/195 |
| 4,846,811 | A | 7/1989 | Vanderhoof ................. 604/263 |

(Continued)

FOREIGN PATENT DOCUMENTS

| EP | 0 702 972 B1 | 7/1995 |
| EP | 0 750 915 A2 | 1/1997 |
| EP | 1 027 903 A1 | 8/2000 |
| EP | 1 110 571 A1 | 6/2001 |
| EP | 1 112 754 A1 | 7/2001 |
| EP | 1 374 772 A1 | 1/2004 |
| WO | WO 97/42989 | 11/1997 |
| WO | WO 01/10488 A1 | 2/2001 |
| WO | WO 01/56642 | 8/2001 |
| WO | WO 02/45786 A2 | 11/2001 |
| WO | WO 03/103757 A1 | 12/2003 |

*Primary Examiner*—Cris L. Rodriguez
(74) *Attorney, Agent, or Firm*—Paul S. Evans

(57) ABSTRACT

A medical needle shield apparatus is provided that includes a shield that is extensible from a retracted position to an extended position to enclose a distal end of a needle. A binding member is disposed within the shield and defines binding surfaces that form an aperture configured for slidable receipt of the needle between the retracted position and the extended position. The binding member includes at least one drag-inducing member extending therefrom that is configured for slidable engagement with the needle between the retracted position and the extended position such that the at least one drag-inducing member engages the needle to create a drag force with the needle. The drag force causes rotation of the binding member relative to a longitudinal axis of the needle such that the binding surfaces engage the needle to prevent slidable movement of the needle in the extended position of the shield. The binding member further includes a retainer extending therefrom such that the retainer is engageable with the needle to prevent rotation of the binding member.

33 Claims, 20 Drawing Sheets

U.S. PATENT DOCUMENTS

| | | | |
|---|---|---|---|
| 4,917,669 A | 4/1990 | Bonaldo | 604/164 |
| 4,929,241 A | 5/1990 | Kulli | 604/263 |
| 4,931,048 A | 6/1990 | Lopez | 604/110 |
| 4,944,725 A | 7/1990 | McDonald | 604/164 |
| 4,950,252 A | 8/1990 | Luther et al. | 604/198 |
| 4,952,207 A | 8/1990 | Lemieux | 604/164 |
| 4,964,854 A | 10/1990 | Luther | 604/166 |
| 4,978,344 A | 12/1990 | Dombrowski | 604/198 |
| 4,994,041 A | 2/1991 | Dombrowski | 604/164 |
| 5,007,901 A | 4/1991 | Shields | 604/110 |
| 5,049,136 A | 9/1991 | Johnson | 604/198 |
| 5,051,109 A | 9/1991 | Simon | 604/263 |
| 5,053,017 A | 10/1991 | Chamuel | 604/192 |
| 5,059,180 A | 10/1991 | McLees | 604/110 |
| 5,084,023 A | 1/1992 | Lemieux | 604/167 |
| 5,084,030 A | 1/1992 | Byrne | 604/198 |
| 5,085,648 A | 2/1992 | Purdy | 604/198 |
| 5,127,905 A | 7/1992 | Lemieux | 604/164 |
| 5,135,504 A | 8/1992 | McLees | 604/164 |
| 5,147,327 A | 9/1992 | Johnson | 604/198 |
| 5,171,229 A | 12/1992 | McNeil | 604/192 |
| 5,183,468 A | 2/1993 | McLees | 604/164 |
| 5,205,829 A | 4/1993 | Lituchy | 604/164 |
| 5,215,528 A | 6/1993 | Purdy | 604/164 |
| 5,300,045 A | 4/1994 | Plassche | 604/263 |
| 5,312,371 A | 5/1994 | Dombrowski | 604/198 |
| 5,322,517 A | 6/1994 | Sircom | 604/198 |
| 5,328,482 A | 7/1994 | Sircom | 604/164 |
| 5,334,158 A | 8/1994 | McLees | 604/110 |
| 5,342,310 A | 8/1994 | Ueyama | 604/110 |
| 5,344,408 A | 9/1994 | Partika | 604/192 |
| 5,348,544 A | 9/1994 | Sweeney | 604/192 |
| 5,411,486 A | 5/1995 | Zadini | 604/198 |
| 5,417,659 A | 5/1995 | Gaba | 604/110 |
| 5,419,766 A | 5/1995 | Chang | 604/110 |
| 5,423,766 A | 6/1995 | Di Cesare | 604/192 |
| 5,458,658 A | 10/1995 | Sircom | 604/164 |
| 5,478,313 A | 12/1995 | White | 604/110 |
| 5,487,733 A | 1/1996 | Caizza et al. | 604/110 |
| 5,531,704 A | 7/1996 | Knotek | 604/192 |
| 5,533,974 A | 7/1996 | Gaba | 604/110 |
| 5,538,508 A | 7/1996 | Steyn | 604/192 |
| 5,549,570 A | 8/1996 | Rogalsky | 604/198 |
| 5,558,651 A | 9/1996 | Crawford | 604/263 |
| 5,562,624 A | 10/1996 | Righi | 604/110 |
| 5,562,633 A | 10/1996 | Wozencroft | 604/171 |
| 5,582,597 A | 12/1996 | Brimhall et al. | 604/192 |
| 5,584,809 A | 12/1996 | Gaba | 604/110 |
| 5,584,810 A | 12/1996 | Brimhall | 604/110 |
| 5,584,818 A | 12/1996 | Morrison | 604/197 |
| 5,599,310 A | 2/1997 | Bogert | 604/164 |
| 5,601,532 A | 2/1997 | Gaba | 604/110 |
| 5,601,536 A | 2/1997 | Crawford | 604/263 |
| 5,611,781 A | 3/1997 | Sircom | 604/164 |
| 5,662,610 A | 9/1997 | Sircom | 604/110 |
| 5,683,365 A | 11/1997 | Brown | 604/110 |
| 5,697,907 A | 12/1997 | Gaba | 604/110 |
| 5,718,688 A | 2/1998 | Wozencroft | 604/164 |
| 5,725,504 A | 3/1998 | Collins | 604/165 |
| 5,749,856 A | 5/1998 | Zadini | 604/162 |
| 5,853,393 A | 12/1998 | Bogert | 604/165 |
| 5,879,337 A | 3/1999 | Kuracina | 604/192 |
| 5,882,337 A | 3/1999 | Bogert | 604/110 |
| 5,910,130 A | 6/1999 | Caizza et al. | 604/110 |
| 5,911,705 A | 6/1999 | Howell | 604/110 |
| 5,951,515 A | 9/1999 | Osterlind | 604/110 |
| 5,980,488 A | 11/1999 | Thorne | 604/110 |
| 6,001,080 A | 12/1999 | Kuracina | 604/171 |
| 6,004,294 A | 12/1999 | Brimhall | 604/164 |
| 6,117,108 A | 9/2000 | Woehr | 604/110 |
| 6,132,401 A | 10/2000 | Van Der Meyden | 604/195 |
| 6,193,694 B1 | 2/2001 | Bell | 604/192 |
| 6,203,527 B1 | 3/2001 | Zadini | 604/110 |
| 6,210,373 B1 | 4/2001 | Allmon | 604/192 |
| 6,221,047 B1 | 4/2001 | Greene et al. | 604/164 |
| 6,280,419 B1 | 8/2001 | Vojtasek | 604/192 |
| 6,287,278 B1 | 9/2001 | Woehr et al. | 604/110 |
| 6,406,459 B1 | 6/2002 | Allmon | 604/192 |
| 6,443,927 B1 | 9/2002 | Cook | 604/110 |
| 6,443,929 B1 | 9/2002 | Kuracina et al. | 604/192 |
| 6,585,704 B1 | 7/2003 | Luther et al. | 604/263 |
| 6,616,630 B1 | 9/2003 | Woehr et al. | 604/110 |
| 6,623,458 B1 | 9/2003 | Woehr et al. | 604/192 |
| 6,629,959 B1 | 10/2003 | Kuracina et al. | 604/192 |
| 6,652,486 B1 | 11/2003 | Bialecki et al. | 604/110 |
| 6,652,490 B1 * | 11/2003 | Howell | 604/110 |
| 6,682,510 B1 | 1/2004 | Niermann | 604/263 |
| 2002/0099339 A1 | 7/2002 | Niermann | 604/263 |
| 2002/0107483 A1 | 8/2002 | Cook | 604/164.01 |
| 2002/0177813 A1 | 11/2002 | Adams et al. | 604/164.07 |
| 2002/0177818 A1 | 11/2002 | Vaillancourt | 604/198 |
| 2003/0036731 A1 | 2/2003 | Wilkinson et al. | 604/198 |
| 2003/0114797 A1 | 6/2003 | Vaillancourt et al. | 604/171 |
| 2003/0135157 A1 | 7/2003 | Saulenas et al. | 604/110 |
| 2003/0144627 A1 | 7/2003 | Woehr et al. | 604/110 |
| 2003/0181875 A1 * | 9/2003 | Bressler et al. | 604/263 |
| 2003/0195471 A1 | 10/2003 | Woehr et al. | 604/164.08 |
| 2003/0195479 A1 | 10/2003 | Kuracine et al. | 604/263 |
| 2003/0216887 A1 | 11/2003 | Hwang | 604/110 |
| 2004/0010227 A1 | 1/2004 | Riesenberger et al. | 604/110 |
| 2004/0049155 A1 * | 3/2004 | Schramm | 604/110 |
| 2004/0049163 A1 * | 3/2004 | Murashita | 604/263 |

* cited by examiner

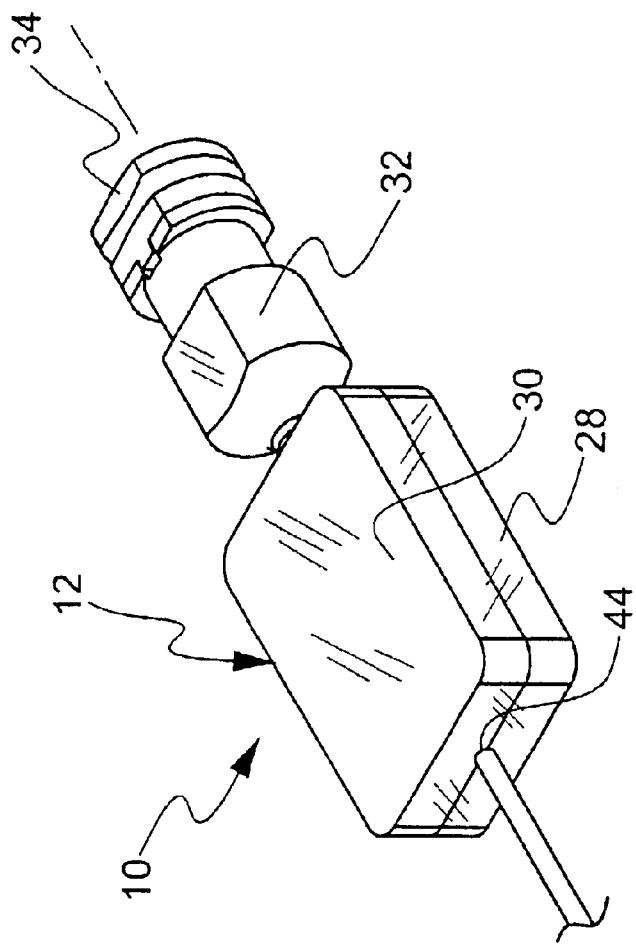
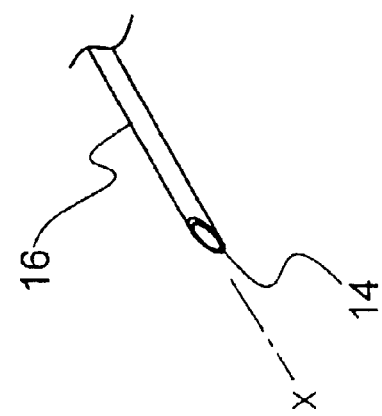
FIGURE 1

SAFETY SHIELD FOR MEDICAL NEEDLES

CROSS REFERENCE TO RELATED APPLICATIONS

This patent application is a continuation-in-part of U.S. Provisional Patent application Ser. No. 60/424,655, filed in the U.S. Patent and Trademark Office on Nov. 7, 2002 by Bagley et al., and U.S. Utility patent application Ser. No. 10/202,201, filed in the U.S. Patent and Trademark Office on Jul. 23, 2002 by Ferguson, which is a continuation-in-part of U.S. Utility patent application Ser. No. 09/809,357, filed in the U.S. Patent and Trademark Office on Mar. 15, 2001 by Ferguson et al. now U.S. Pat. No. 6,595,955, the entire contents of each of these disclosures being hereby incorporated by reference herein.

BACKGROUND

1. Technical Field

The present disclosure generally relates to safety shields for medical needles, and more particularly, to safety shields that protect a needle point of a medical needle.

2. Description of the Related Art

Problems associated with inadvertent needle sticks are well known in the art of blood sampling, percutaneous medication injection and other medical procedures involving use of medical needles. Significant attention has been focused on needle stick problems due to the contemporary sensitivity of exposure to AIDS, Hepatitis and other serious blood-borne pathogen exposures.

Procedures for removing a needle from a patient commonly require a technician to use one hand to place pressure at the wound site where the needle is being withdrawn, while removing the needle device with the other hand. It is also common practice for an attending technician to give higher priority to care for the wound than is given to disposal of a needle. In the case of typical needle devices without safety shields, such priority either requires the convenience of an available sharps container within reach or another means for safe disposal without leaving the patient's side. Providing adequate care while following safety procedures is often compounded by the patient's physical condition and mental state, such as in burn units and psychiatric wards. Under such conditions, it is difficult to properly dispose of a used needle while caring for a patient.

The widespread knowledge and history associated with needle care and disposal problems have resulted in numerous devices for preventing accidental needle sticks. Problems of current safety devices include difficulty of use and high cost due to their complexity and number of parts.

Other known devices employ sheaths that are spring activated, telescoping, pivoting, etc. These devices, however, may disadvantageously misfire or be cumbersome to activate. Further drawbacks of current devices include high manufacturing cost due to complexity and the number of parts. Thus, these type prior art devices may not adequately and reliably shield medical needle apparatus to prevent hazardous exposure.

Consequently, there remains a need to provide a more satisfactory solution for needle safety devices by overcoming the disadvantages and drawbacks of the prior art. Therefore, it would be desirable to provide a more adequate and reliable medical needle shield apparatus which employs a safety shield slidably movable along a medical needle to prevent hazardous exposure to a needle tip. Such a needle shield apparatus should be easily and reliably movable to shield a needle tip of a needle cannula.

SUMMARY

Accordingly, the present disclosure addresses a need for a medical needle shield apparatus which effectively and inexpensively protects a tip of a medical needle after use. The present disclosure resolves related disadvantages and drawbacks experienced in the art. More specifically, the apparatus and method of this invention constitute an important advance in the art of safety needle devices.

In one particular embodiment, a medical needle shield apparatus is provided in accordance with the principles of the present disclosure. The medical needle shield apparatus includes a shield that is extensible from a retracted position to an extended position to enclose a distal end of a needle. A binding member is disposed within the shield and defines binding surfaces that form an aperture configured for slidable receipt of the needle between the retracted position and the extended position. The binding member includes at least one drag inducing member that is configured for slidable engagement with the needle between the retracted position and the extended position such that the at least one drag inducing member engages the needle to create a drag force with the needle. The drag force facilitates rotation, as will be discussed, of the binding member relative to a longitudinal axis of the needle such that the binding surfaces engage the needle to prevent slidable movement of the needle in the extended position of the shield. The binding member further includes a retainer extending therefrom such that the retainer is engageable with the needle to prevent rotation of the binding member.

The binding member may include a substantially planar aperture plate that has the binding surfaces that form the aperture. The aperture plate may be substantially perpendicular relative to the longitudinal axis of the needle due to engagement of the retainer with the needle.

Alternatively, the retainer includes a first portion extending from the binding member and a second portion extending from the first portion. The first portion can extend from the binding member in substantially parallel alignment with the needle due to engagement of the retainer with the needle. The second portion can extend transversely relative to the longitudinal axis of the needle and is configured for engagement with the needle. The second portion may have a substantially planar portion for engagement with the needle. The substantially planar portion of the second portion may define a retainer cavity.

The at least one drag inducing member may include the aperture of the binding member such that the aperture engages the needle to create the drag force with the needle. The at least one drag inducing member may include a pair of friction members that extend to engage the needle to create the drag force with the needle. The pair of friction members may define a cavity that is substantially aligned with the aperture. The cavity is configured for slidable receipt of the needle to create the drag force with the needle.

Alternatively, the binding member is rotatable, relative to the longitudinal axis of the needle, between a non-binding orientation whereby the needle is slidable relative to the binding member and a binding orientation whereby the binding surfaces engage the needle to prevent slidable movement of the needle in the extended position of the shield. The shield may include a housing that defines at least one blocking member extending from an interior surface thereof. The at least one blocking member is engageable with the binding member for urging the binding member to the binding orientation.

In an alternate embodiment, the medical needle shield apparatus includes an outer rotatable housing that encloses the shield. The outer rotatable housing supports the shield for relative rotational movement therewith in the extended position of the shield. The shield may be supported for relative rotational movement by the outer rotatable housing by at least one bearing.

BRIEF DESCRIPTION OF THE DRAWINGS

The foregoing and other features and advantages of the present invention will be more fully understood from the following detailed description of the exemplary embodiments, taken in conjunction with the accompanying drawings in which:

FIG. 1 is a perspective view of one particular embodiment of a medical needle shield apparatus in accordance with the principles of the present disclosure;

DETAILED DESCRIPTION OF THE EXEMPLARY EMBODIMENTS

Figure 2:
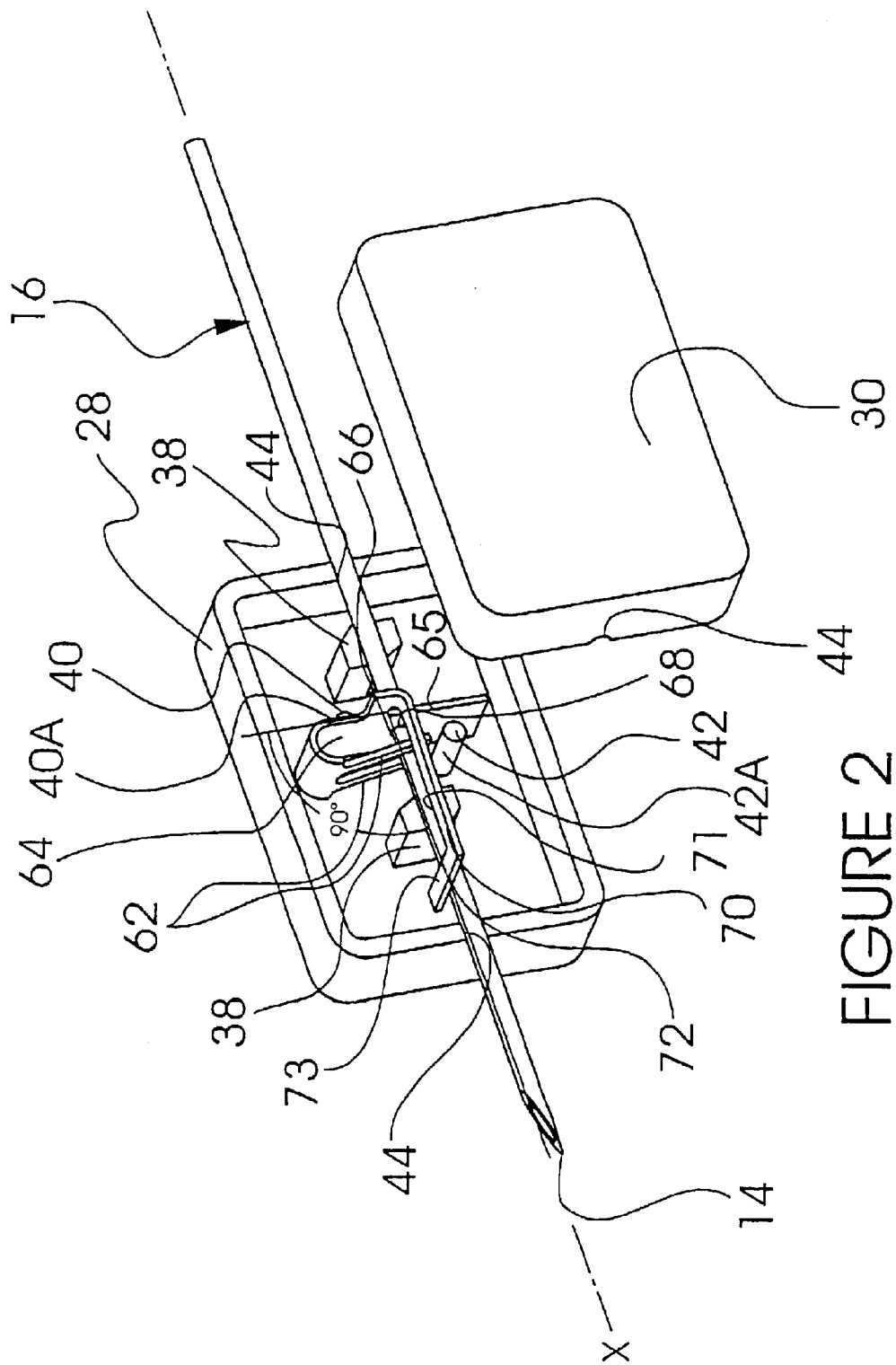
FIG. 2 is a cutaway perspective view of a shield and a needle, in a non-binding orientation, of the medical needle shield apparatus shown in FIG. 1 with a housing section separated.

The exemplary embodiments of the medical needle shield apparatus and methods of operation disclosed are discussed in terms of medical needles for infusion of intravenous fluids, medication infusion or fluid collection, and more particularly, in terms of needle shield apparatus employed with a needle cannula that prevent hazardous exposure to the needle tip, including, for example, inadvertent needle sticks. It is envisioned that the present disclosure, however, finds application to a wide variety of cannula needles and devices for the infusion of preventive medications, medicaments, therapeutics, etc. to a subject. It is also envisioned that the present disclosure may be employed for collection of body fluids including those employed during procedures relating to phlebotomy, digestive, intestinal, urinary, veterinary, etc. It is contemplated that the medical needle shield apparatus may be utilized with other medical needle applications including, but not limited to, fluid infusion, fluid collection, catheters, catheter introducers, guidewire introducers, spinal and epidural, biopsy, aphaeresis, dialysis, blood donor, Veress needles, Huber needles, etc.

In the discussion that follows, the term "proximal" refers to a portion of a structure that is closer to a clinician, and the term "distal" refers to a portion that is further from the clinician. As used herein, the term "subject" refers to a patient that receives infusions or has blood and/or fluid collected therefrom using the medical needle shield apparatus. According to the present disclosure, the term "clinician" refers to an individual administering an infusion, performing fluid collection, installing or removing a needle cannula from a medical needle shield apparatus and may include support personnel.

The following discussion includes a description of the medical needle shield apparatus, followed by a description of the method of operating the medical needle shield apparatus in accordance with the present disclosure. Reference will now be made in detail to the exemplary embodiments of the disclosure, which are illustrated in the accompanying figures.

Turning now to the figures, wherein like components are designated by like reference numerals throughout the several views. Referring initially to FIGS. 1–4, there is illustrated a medical needle shield apparatus, constructed in accordance with the principals of the present disclosure. The medical needle shield apparatus includes a shield 10 that is extensible from a retracted position (FIG. 1) to an extended position (FIG. 3) to enclose a distal end 14 of a needle such as, for example, elongated needle cannula 16.

A binding member 64 is disposed within shield 10 and defines binding surfaces 68. Binding surfaces 68 form an aperture 66 configured for slidable receipt of needle cannula 16 between the retracted position and the extended position. Binding member 64 includes a drag inducing member, such as, for example, friction members 62 extending therefrom. Binding member 64 includes a retainer 70 extending therefrom. Retainer 70 is engageable with needle cannula 16 to prevent rotation of binding member 64. Friction members 62 are configured for slidable engagement with needle cannula 16 between the retracted position and the extended position such that friction members 62 engage needle cannula 16 to create a drag force with needle cannula 16. It is envisioned that one or a plurality of friction members 62 may be employed. The drag force in conjunction with one of the blocking members 40 or 42, cause binding member 64 to move to the binding position. Note that the force created by blocking member 40 or 42 acts in a direction opposite of the drag force. This causes a force couple, which moves the binding member 64 to the binding position. As needle 16 is released from engagement with needle communicating surface 72, binding member 64 and retainer 70 move to the binding position. Rotation is no longer opposed by engagement with needle 16 at needle communicating surface 72. Thus, binding member 64, attached to retainer 70, is subject to inclination into a binding orientation. Rotation of binding member 64 causes binding surfaces 68 to frictionally engage needle 16 to prevent movement thereof. Blocking member 40 or 42 cause binding member 64 to move to the binding position as forces are imposed on shield 10 in either direction along longitudinal axis x. This maintains needle 16 within shield 10 to avoid hazardous exposure to distal end 14. It is envisioned that needle communicating surface 72 may include ribs, projections, cavities, etc. for engagement with needle 16 or that a portion of needle communicating surface 72 engages needle 16.

The components of the medical needle shield apparatus can be fabricated from a material suitable for medical applications, such as, for example, polymerics or metals, such as stainless steel, depending on the particular medical application and/or preference of a clinician. Semi-rigid and rigid polymerics are contemplated for fabrication, as well as resilient materials, such as molded medical grade polypropylene. However, one skilled in the art will realize that other materials and fabrication methods suitable for assembly and manufacture, in accordance with the present disclosure, also would be appropriate.

Shield 10 includes a housing 12 that encloses binding member 64. Housing 12 includes a housing first section 28 and a housing second section 30. It is envisioned that housing sections 28, 30 may be variously configured and dimensioned such as, for example, rectangular, spherical, etc. It is further envisioned that housing sections 28, 30 may be joined by any appropriate process such as, for example, snap fit, adhesive, solvent weld, thermal weld, ultrasonic weld, screw, rivet, etc. Alternatively, housing 12 may be monolithically formed or integrally assembled of multiple housing sections and may be substantially transparent, opaque, etc. Housing sections 28 may include ribs, ridges, etc. to facilitate manipulation of the medical needle shield apparatus.

Housing 12 includes openings 44, disposed at proximal and distal end thereof, that are configured and dimensioned to allow needle cannula 16 to freely pass through. In the retracted position, shield 10 is disposed adjacent to a hub 32 of a medical needle. The medical needle may include a stylet 34 within the bore of the needle. It is contemplated that the components of the medical needle apparatus may be employed with other needle applications, such as, for example, catheters, guidewire introducers, such as a Seldinger needle, etc.

Binding member 64 may be monolithically formed and includes an aperture plate 65, frictional members 62, and retainer 70, which includes end sensing member 71 and needle communicating surface 72. It is contemplated that binding member 64 may include one or more frictional members 62. Aperture plate 65 has a rectangular, generally planar configuration with sufficient stiffness to produce forces for binding needle cannula 16, as will be discussed. It is envisioned that aperture plate 65 may have an arcuate surface, undulating, etc. It is further envisioned that aperture plate 65 may have various degrees of stiffness according to the requirements of a particular application.

Frictional members 62 may be monolithically formed with binding member 64 and extend from aperture plate 65 in association therewith for alignment with aperture 66 and engagement with needle cannula 16. Each frictional member 62 includes a flexible arm 62A, which are spaced apart to facilitate sliding engagement with needle cannula 16. Such engagement creates a frictional drag force with needle cannula 16. This frictional drag force in conjunction with one of the blocking members 40 or 42 causes binding member 64 to move with needle cannula 16, which generates a canting force in retainer 70 and inclination of aperture plate 65. The canting force and inclination urge rotation of binding member 64. It is contemplated that a single friction member may be employed. It is further contemplated that frictional members 62 may have flexible portions, which may be of varying flexibility according to the particular requirements of a needle application.

As facilitated by movement of needle cannula 16, the canting force causes a lever or moment of retainer 70, which is opposed to prevent rotation of binding member 64. The canting force is opposed by engagement of needle communicating surface 72 with needle cannula 16 in a non-binding or sliding orientation of binding member 64.

End sensing member 71 extends distally from aperture plate 65, parallel to needle cannula 16. End sensing member 71 may be perpendicularly oriented relative to a plane defined by aperture plate 65. This perpendicular orientation facilitates inclination of aperture plate 64 for disposal in a binding or non-binding orientation of binding member 64. It is envisioned that end sensing member 71 may be variously oriented with aperture plate 65 and may flexibly extend therefrom.

Needle communicating surface 72 opposes the canting force of end sensing member 71 directed to needle cannula 16. The canting force is generated by friction members 62 in conjunction with one of the blocking members 40 or 42 and facilitates inclination of aperture plate 65. Inclination, however, is prevented in the non-binding or sliding orientation because of the engagement of needle communicating surface 72 with needle cannula 16. As needle cannula 16 is retracted proximally and shield 10 is extended distally, needle cannula 16 continues to slideably engage needle communicating surface 72.

Figure 3:
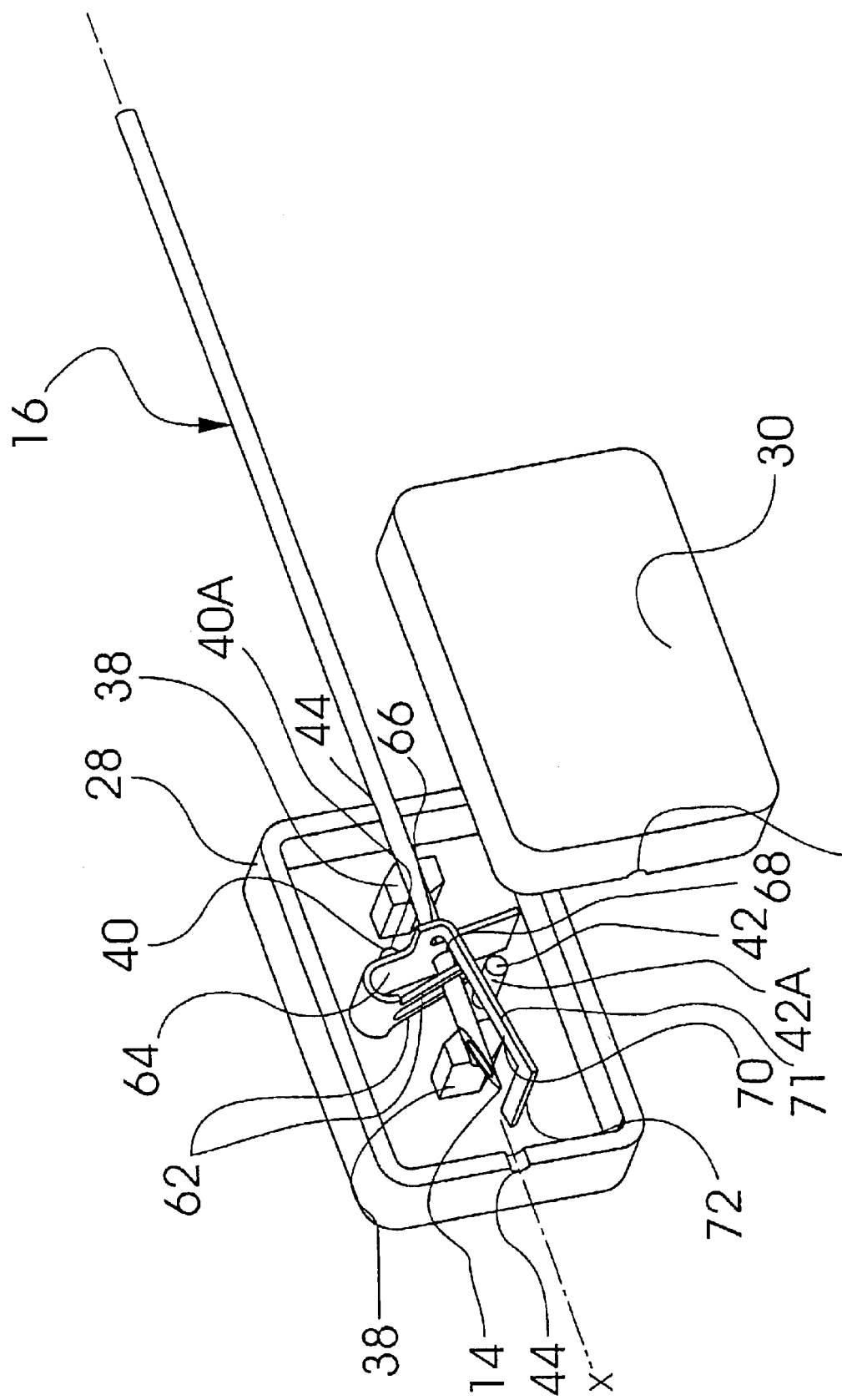
FIG. 3 is a cutaway perspective view of the shield and the needle, in a binding orientation, of the medical needle shield apparatus shown in FIG. 1 with the housing section separated.
Figure 4:
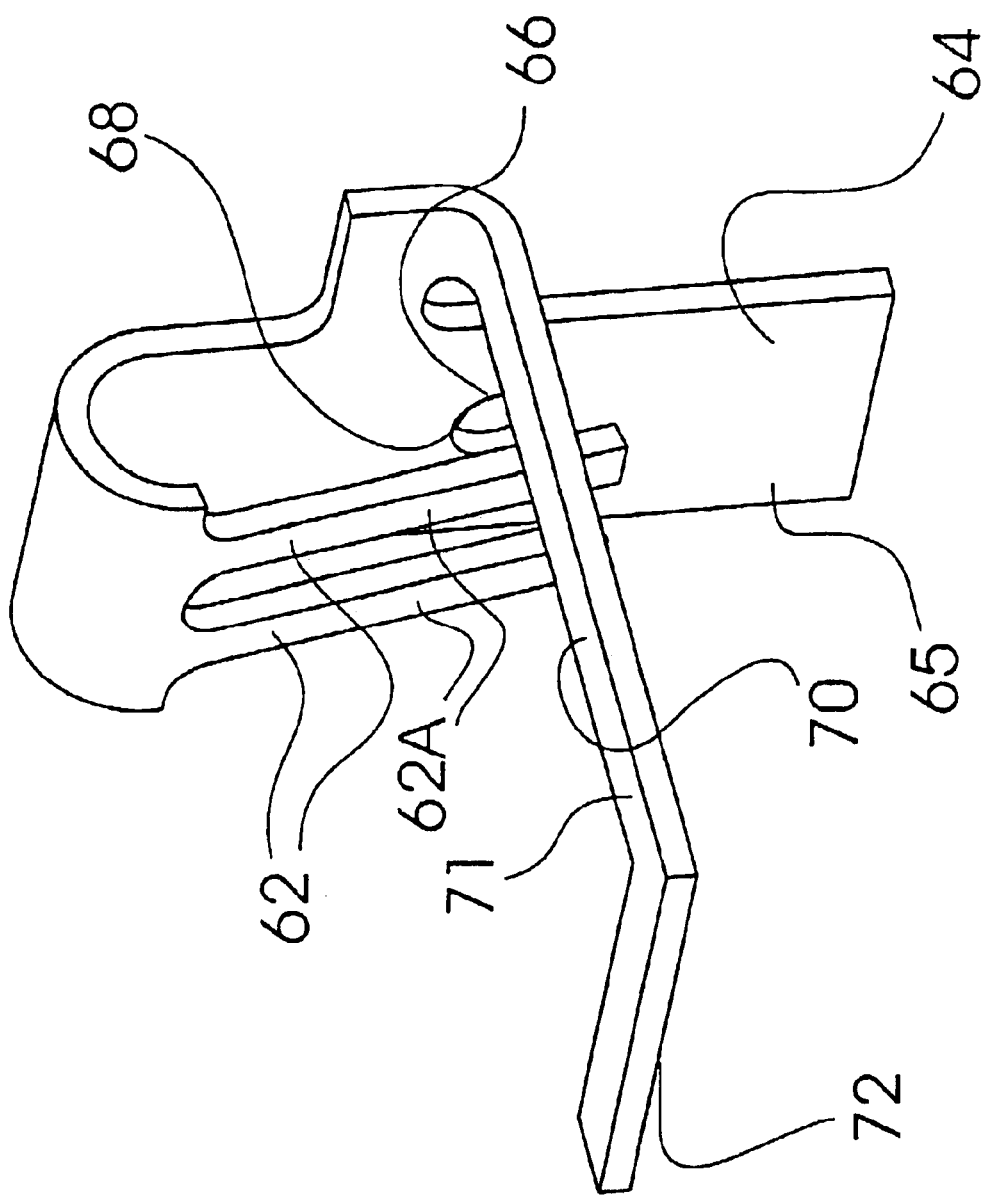
FIG. 4 is an enlarged perspective view of a binding member of the medical needle shield apparatus shown in FIG. 1.

As needle cannula 16 is released from engagement with needle communicating surface 72, as shown in FIG. 3, a drag force is created between friction members 62 and needle cannula 16. The drag force in conjunction with blocking member 42, cause aperture plate 65 to move to the binding position. Note that the force created by blocking member 42 acts in a direction opposite of the drag force. This causes a force couple which moves the aperture plate 65 to the binding position. As needle cannula 16 is released from engagement with the needle communicating surface 72, aperture plate 65 moves to the binding position. Rotation is no longer opposed by engagement with needle cannula 16 at needle communicating surface 72. Thus, aperture plate 65, attached to retainer 70, is subject to inclination into a binding orientation. Rotation of aperture plate 65 causes binding surfaces 68 to frictionally engage needle cannula 16 to prevent movement thereof. Blocking members 40, 42 cause aperture plate 65 to move to the binding position as forces are imposed on shield 10 in either direction along longitudinal axis x. This maintains needle cannula 16 within shield 10 to avoid hazardous exposure to distal end 14. It is further envisioned that needle communicating surface 72 may include ribs, projections, cavities, etc. for engagement with needle cannula 16 or that a portion of needle communicating surface 72 engages needle cannula 16.

Aperture 66 is formed within aperture plate 65 for slidable engagement with needle cannula 16 during movement between the retracted position and the extended position of shield 10. Aperture 66 includes binding surfaces 68 formed on opposing sides of aperture 66 that engage needle cannula 16 to prevent movement thereof in the extended position of shield 10. It is contemplated that engagement to prevent movement of needle cannula 16 may include penetrating, frictional, interference, etc. It is envisioned that aperture 66 may have various geometric configurations, such as radial, polygonal, etc. It is further envisioned that aperture 66 may define an open cavity within aperture plate 65, such as, for example, "U" shaped and open to one or a plurality of edges of aperture plate 65.

The inclination of aperture plate 65 relative to longitudinal axis x facilitates sliding and binding, via binding surfaces 68 of aperture 66, of needle cannula 16 within shield 10 to prevent hazardous exposure to distal end 14. For example, as shown in FIG. 2, aperture plate 65 is oriented at an angle of approximately 90° relative to longitudinal axis x such that aperture plate 65 is disposed substantially perpendicular to needle cannula 16. In this non-binding or sliding orientation, needle cannula 16 is free to slide within aperture 66. As needle cannula 16 is retracted and shield 10 is extended, needle cannula 16 continues to engage needle communicating surface 72 and aperture plate 65 maintains its perpendicular orientation relative to longitudinal axis x.

Referring to FIG. 3, shield 10 is manipulated such that friction members 62 in conjunction with blocking member 42 cause binding member 64 to rotate relative to longitudinal axis x. Aperture plate 65 rotates out of perpendicular alignment with needle cannula 16 such that aperture plate 65 is oriented at an angle a, which is less than 90° with respect to longitudinal axis x. It is contemplated that angle a may be measured from either side of aperture plate 65.

Aperture plate 65 rotates to angle a and binding member 64 approaches a binding orientation. The binding orientation includes engagement of binding surfaces 68 with needle cannula 16 due to the binding orientation of aperture plate 65. This engagement creates binding frictional forces on needle cannula 16, in conjunction with frictional members 62 and blocking members 40, 42 to prevent movement of needle cannula 16 relative to shield 10 in both distal and proximal directions, and to maintain distal end 14 within shield 10 to prevent hazardous exposure thereto. Blocking members 40, 42 may be formed with one or both of housing sections 28 and 30, and are disposed not to interfere with needle cannula 16. Blocking members 40, 42 define surfaces 40A, 42A respectively, that facilitate disposal of aperture plate 65 in a binding orientation.

For example, as shown in FIG. 2, shield 10 is in a retracted position and needle cannula 16 is fully extended. Binding member 64 and aperture plate 65 are in a non-binding or sliding orientation such that aperture plate 65 is substantially perpendicular to longitudinal axis x. Blocking members 40, 42 may engage aperture plate 65 to maintain aperture plate 65 in the perpendicular orientation. Blocking members 40, 42 may also maintain such orientation during extension of needle cannula 16 or may not engage needle cannula 16.

As needle cannula 16 is retracted and shield 10 is extended, friction members 62 create a drag force via engagement with needle cannula 16 on binding member 64 and in conjunction with blocking member 42 cause aperture plate 65 to rotate in a counter-clockwise direction to the binding orientation. Blocking member surfaces 40A, 42A engage aperture plate 65 to facilitate rotation thereof from the perpendicular orientation into the binding orientation such that binding surfaces 68 engage needle cannula 16. This configuration prevents movement of needle cannula 16.

Housing 12 may also include needle supports 38 that guide needle cannula 16 during axial movement thereof. Needle supports 38 laterally engage needle cannula 16 to maintain axial alignment during passage through shield 10. It is envisioned that one or a plurality of needle supports 38 may be used. It is further envisioned that needle supports 38 may define cavities, etc. for slidable receipt of needle cannula 16. Needle Supports 38 may be monolithically formed in conjunction with blocking members 40,42.

Binding of binding member 64 to needle cannula 16 is facilitated by the friction force generated between binding surfaces 68 and needle cannula 16. This frictional engagement prevents axial movement of needle cannula 16 relative to housing 12 when shield 10 is in the extended position. This configuration advantageously prevents hazardous exposure to needle cannula 16. It is contemplated that binding surfaces 68 may include sharp edges to increase frictional engagement. It is further contemplated that the binding friction force may be varied by altering factors, such as, for example, aperture 66 dimension, needle cannula 16 diameter, aperture plate 65 thickness, the dimension from blocking members 40, 42 contact point to the centerline of needle cannula 16 and the coefficient of friction between aperture 66 and needle cannula 16 depending on the particular requirements of a needle application. It is envisioned that the friction members 62 may be configured so as to vary the drag force with variation of the inclination of the aperture plate 65, this variation in drag force may be accomplished by geometric changes in the shape of the friction members 62, such as wedge shapes or the inclusion of notches to engage the needle 16, this variation in drag force may also be accomplished through the selective application of friction modifying materials or coatings such as oils, greases, or coatings which increase friction.

Figure 5:
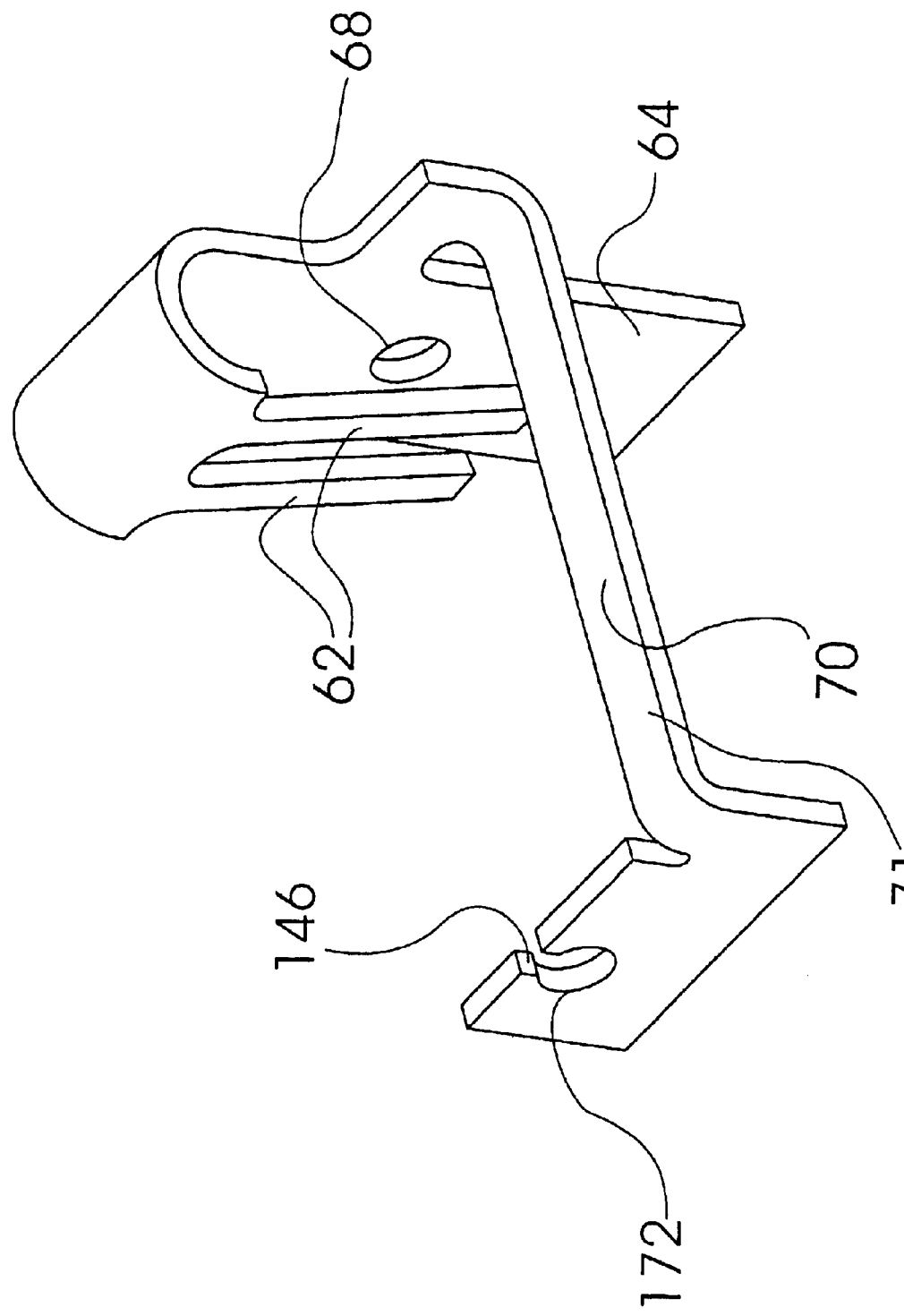
FIG. 5 is an enlarged perspective view of an alternate embodiment of the binding member shown in FIG. 4.

Referring to FIG. 5, an alternate embodiment of binding member 64 is shown. Retainer 70 includes a needle communicating surface 172. Needle communicating surface 172 defines a slot 146 that supportingly engages needle cannula 146. It is contemplated that slot 146 is configured and dimensioned to release a guidewire, which passes through needle cannula 16, both of which pass through shield 10. Slot 146 engages needle cannula 16 and maintains the non-binding or sliding orientation of aperture plate 65 by opposing the canting force of end sensing member 71. Slot 146 may be sized such that the guidewire is not capable of engaging the end sensing member such that as needle cannula 16 is released from engagement with slot 146, sensing member 71 is free to rotate with binding member 64 to the binding orientation unhindered by the guidewire.

Figure 6:
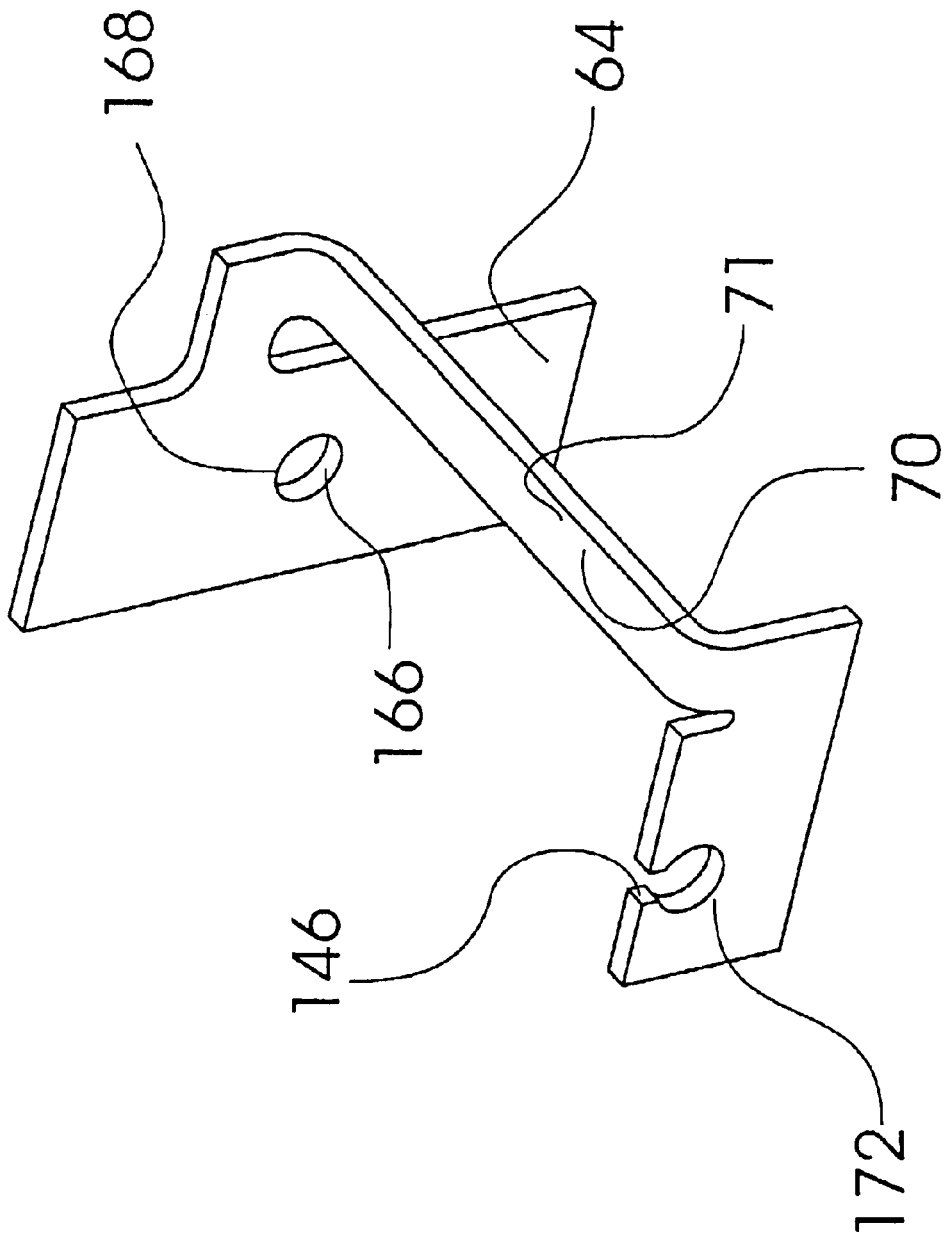
FIG. 6 is an enlarged perspective view of another alternate embodiment of the binding member shown in FIG. 4.
Figure 7:
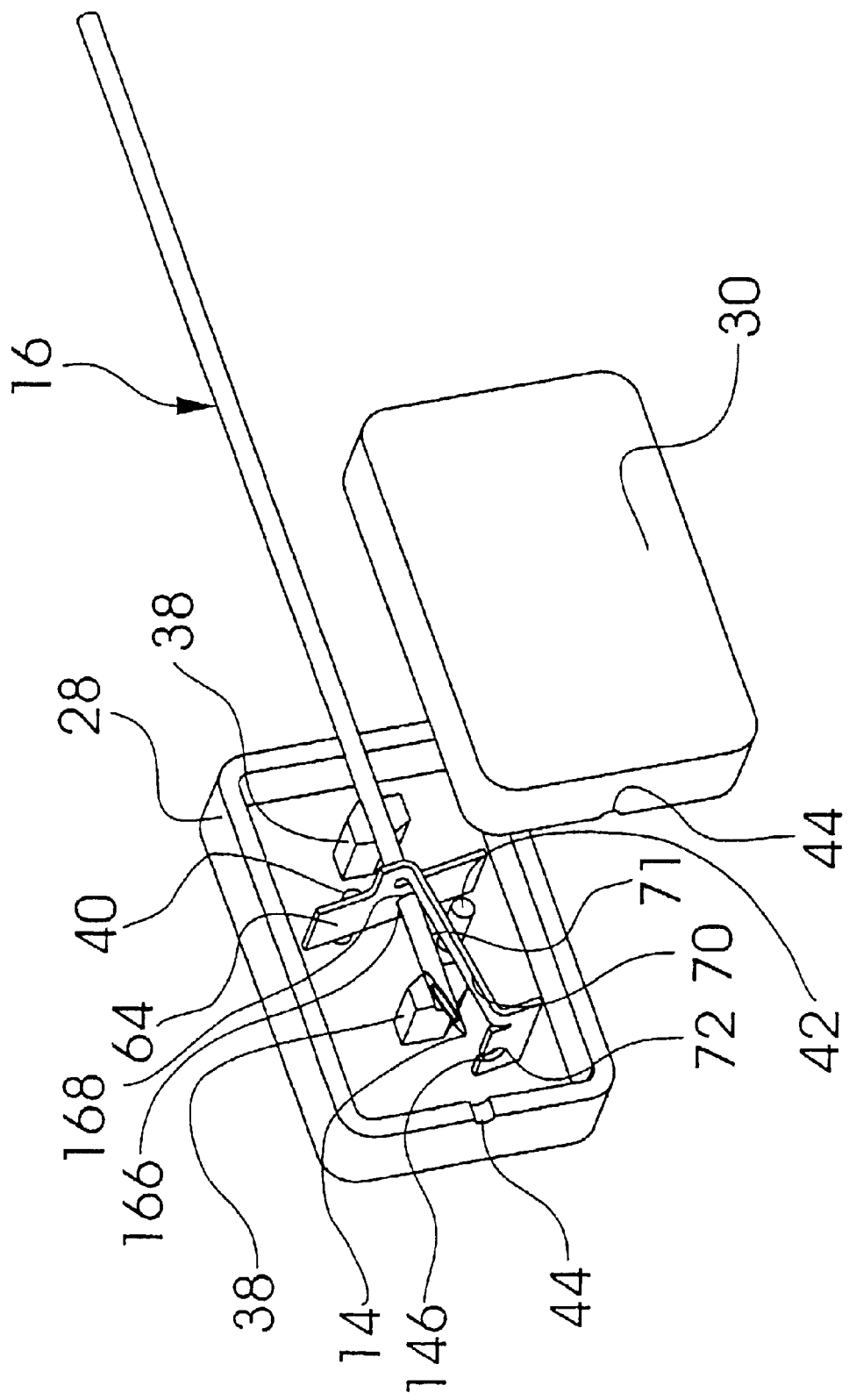
FIG. 7 is a cutaway perspective view of the shield and the needle of the medical needle shield apparatus shown in FIG. 1 employing the binding member shown in FIG. 6.

Referring to FIGS. 6 and 7, another alternate embodiment of binding member 64 is shown. Binding member 64 includes a drag inducing member, such as aperture 166 that is formed by binding surfaces 168. Aperture 166 facilitates sliding engagement with needle cannula 16. Such engagement creates a frictional drag force with needle cannula 16. This frictional drag force in conjunction with blocking member 42 causes binding member 64 to move with needle cannula 16. In a non-binding or sliding orientation of binding member 64, aperture plate 65 engages one of the blocking members 40, 42 causing a canting force in end sensing member 71, as discussed.

Retainer 70 includes a needle communicating surface 172, similar to that described with regard to FIG. 5, which opposes the canting force of end sensing member 71. Slot 146 engages and maintains needle cannula 16 in the non-binding or sliding orientation. As needle cannula 16 is released from engagement with slot 146, binding member 64 is caused to rotate as facilitated by one of the blocking members 40, 42, counter-clockwise to the binding orientation. Binding of binding member 64 to needle cannula 16 is facilitated by the friction force generated between binding surfaces 168 and needle cannula 16. This frictional engagement prevents axial movement of needle cannula 16 in the extended position and prevents hazardous exposure thereto.

Figure 6A:
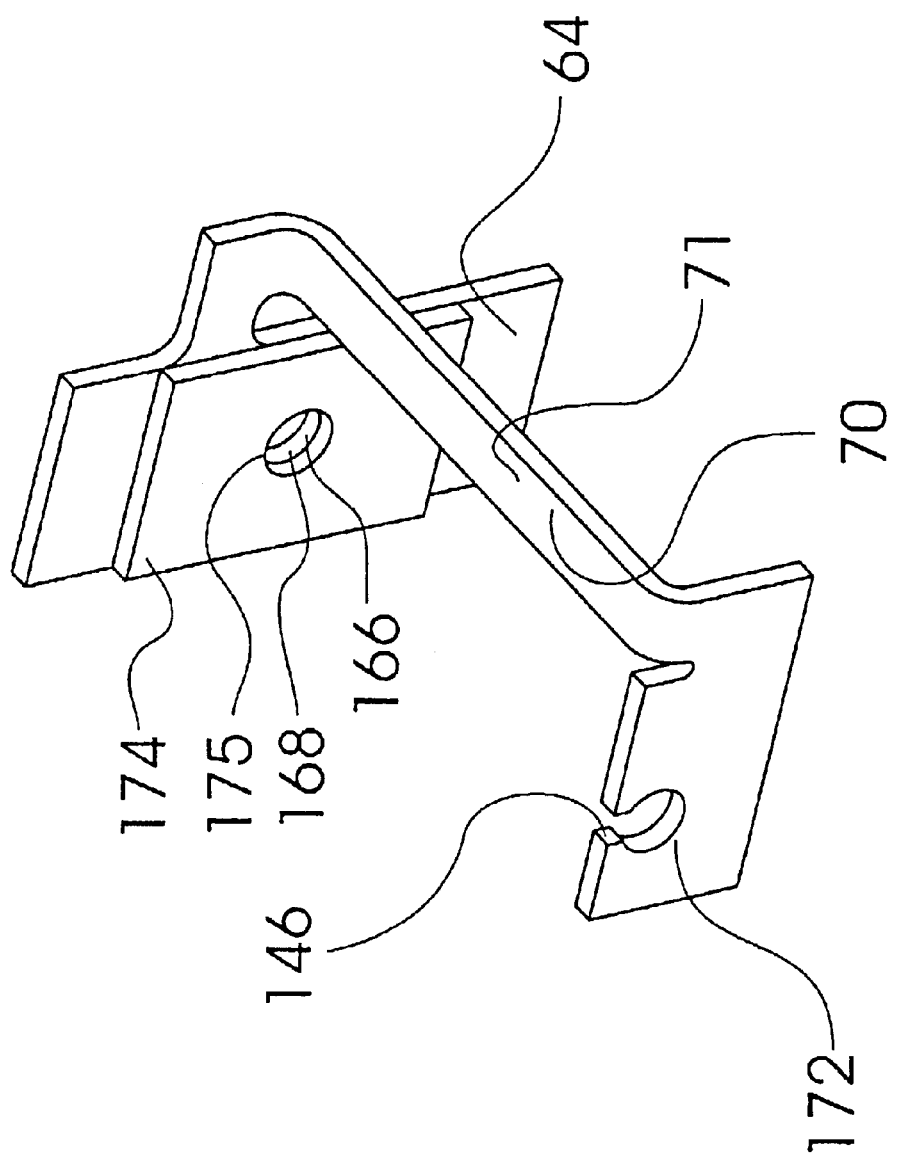
FIG. 6A is an enlarged perspective view of another alternate embodiment of the binding member shown in FIG. 4.
Figure 6B:
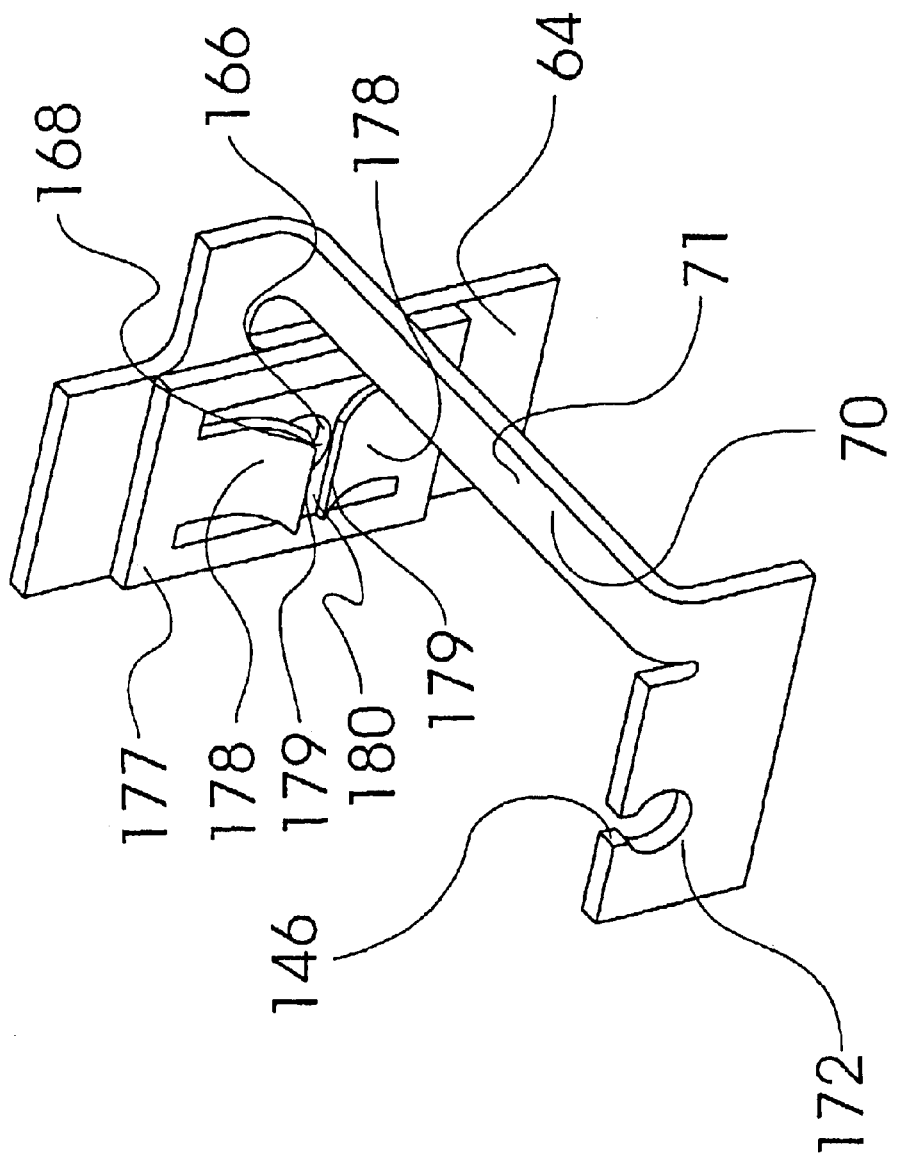
FIG. 6B is an enlarged perspective view of another alternate embodiment of the binding member shown in FIG. 4.

Referring to FIGS. 6A and 6B, alternate embodiments of binding member 64 are shown. FIG. 6A shows a member 174 having a drag opening 175, with member 174 being disposed on binding member 64. The diameter of drag opening 175 is sized so as to create a drag force in conjunction with the needle 16 and in conjunction with one of the blocking members 40 or 42, causing binding member 64 to move to the binding position. It is contemplated that members 174 and 177 may be fabricated from materials such as polymerics, metals, elastomeric materials, etc.

FIG. 6B shows a member 177 having elements 178 defining an opening 180, with member 177 being disposed on binding plate 64. Member 177 includes a drag inducing member, such as opening 180 that is formed by surfaces 179. The distance between surfaces 179 is sized so as to create a drag force in conjunction with the needle 16. Surfaces 179 facilitate sliding engagement with needle cannula 16. Such engagement creates a frictional drag force with needle cannula 16, and in conjunction with one of the blocking members 42 or 43, causing binding member 64 to move to the binding position. It is contemplated that members 174 and 177 may be fabricated from materials such as polymerics, metals, elastomeric materials, etc.

Figure 8:
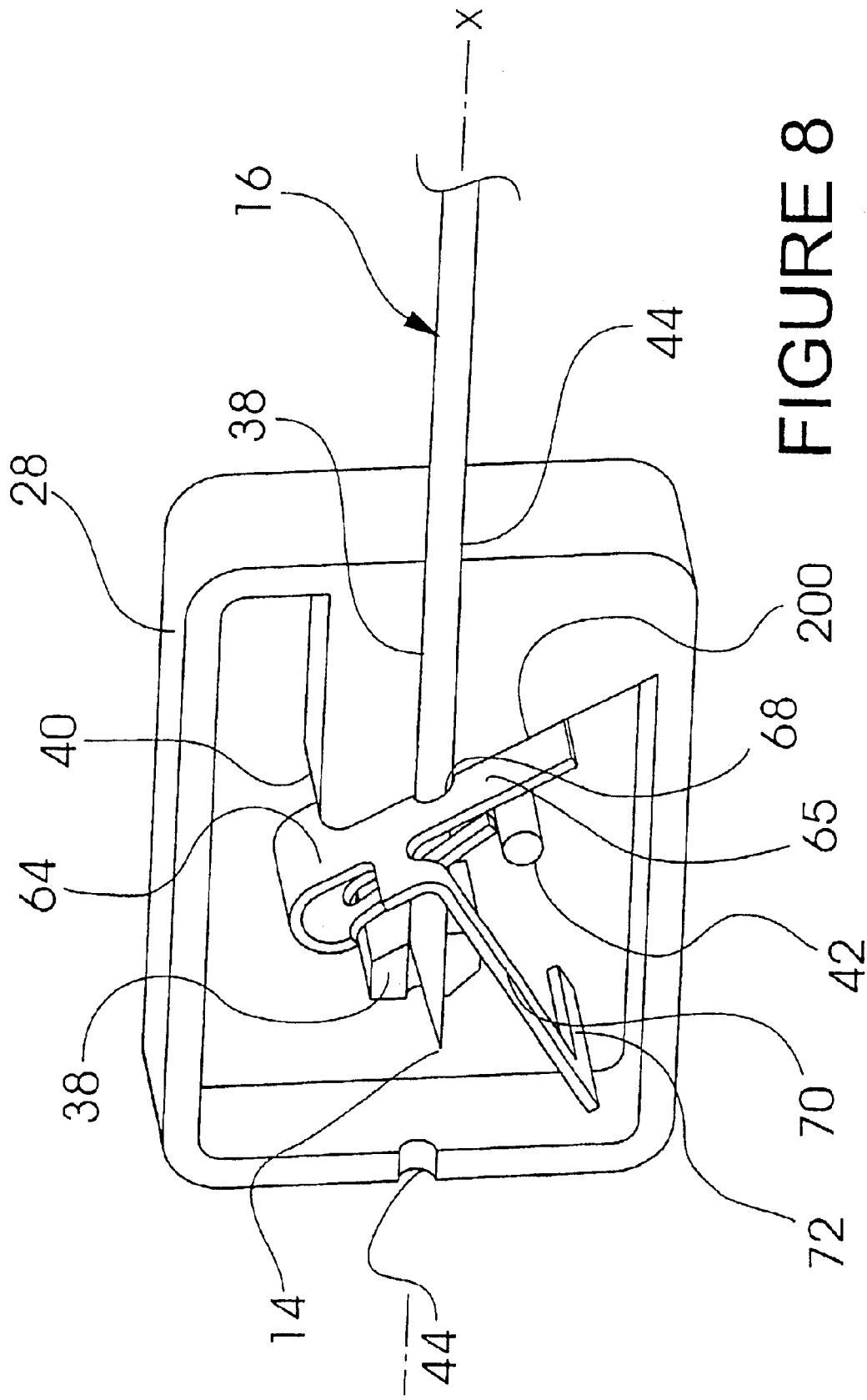
FIG. 8 is an enlarged perspective view of an alternate embodiment of the shield shown in FIG. 2, with a housing section removed.
Figure 9:
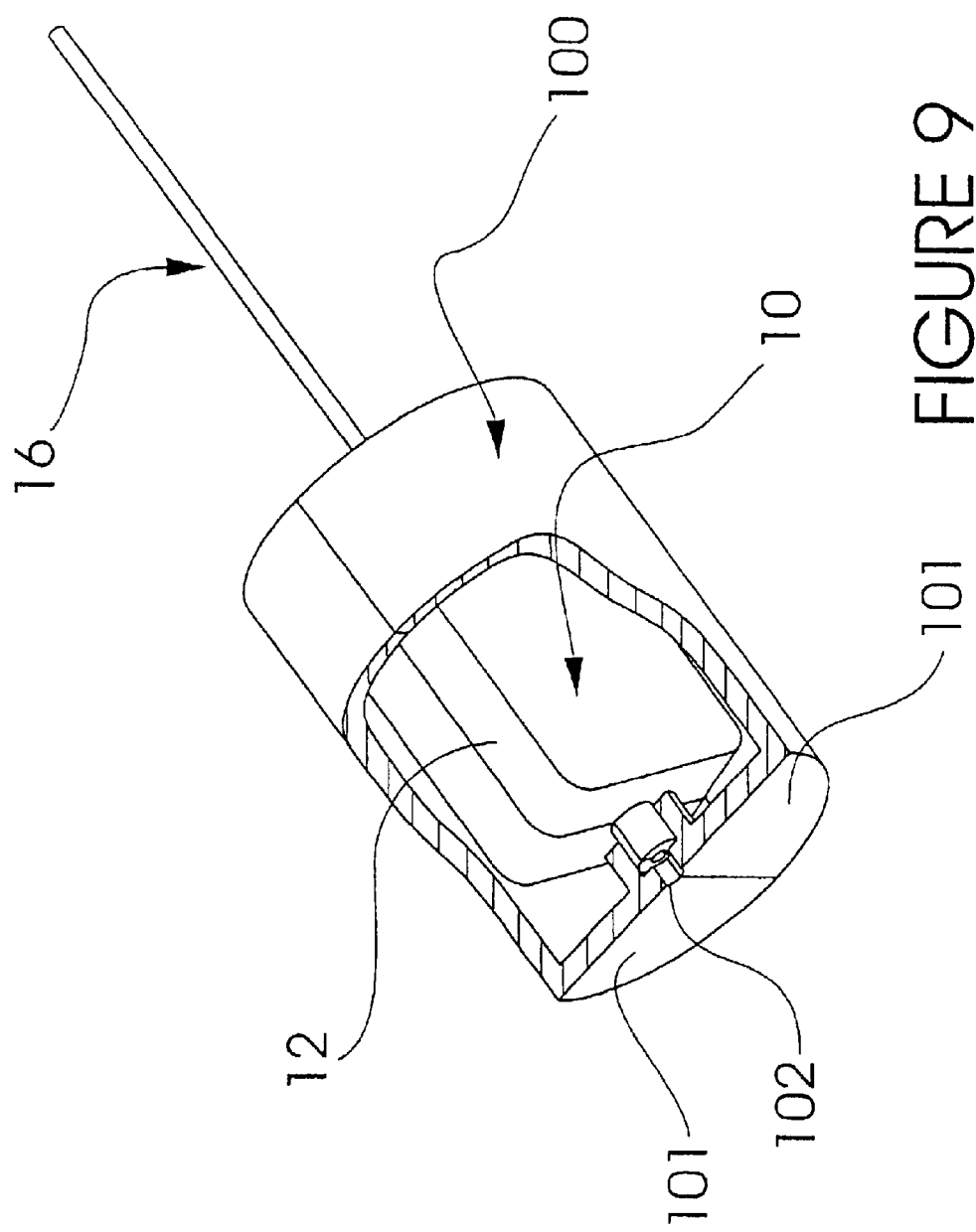
FIG. 9 is a cutaway perspective view of the medical needle shield apparatus shown in FIG. 1 with an outer rotatable housing mounted with the shield and the needle.
Figure 10:
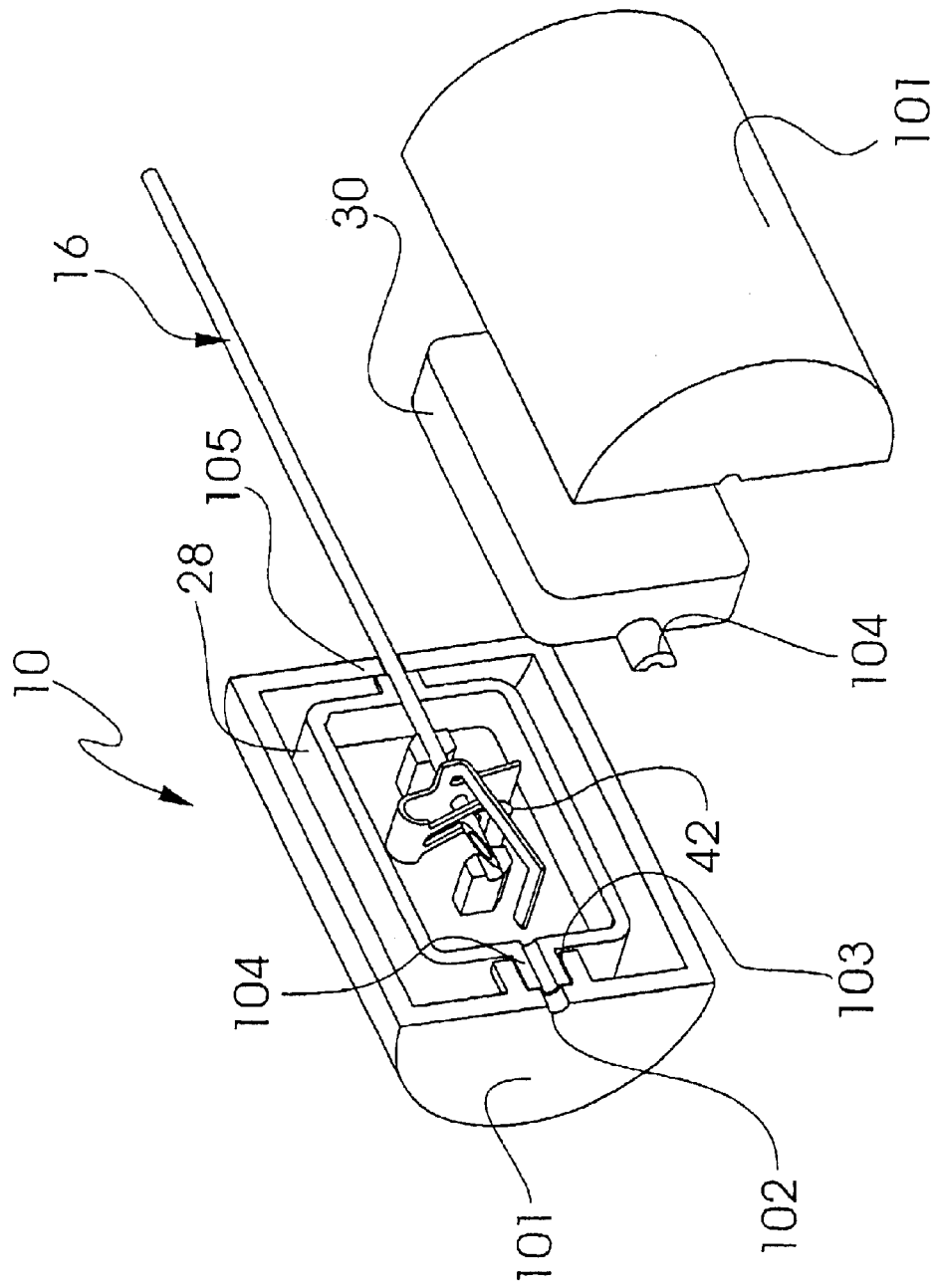
FIG. 10 is a cutaway perspective view of the shield, needle and the outer rotatable housing shown in FIG. 9 with parts separated.

Referring to FIG. 8, an alternate embodiment of housing 12 is shown. Housing 12 includes a plate support surface 200. Plate support surface 200 is formed with one or both housing sections 28, 30. Plate support surface 200 is oriented at an angle relative to longitudinal axis x. Plate support surface 200 is oriented such that, subsequent to binding needle cannula 16 with binding surfaces 68, surface 200 engages aperture plate 65 to prevent structural failure of binding member 64 in the binding orientation. Structural failure of aperture plate 65 includes elastic flexing, plastic failure, etc. It is contemplated that plate support surface 200 may be oriented at various angles, such as, for example, 35–40 degrees. It is further contemplated that plate support surface 200 may be monolithically formed or integrally assembled with housing 12.

In operation, the medical needle shield apparatus, similar to that described in accordance with the principles of the present disclosure is provided for employment with stylet 34. Other needle applications and methods of use are also contemplated. The components of the medical needle shield apparatus are fabricated, properly sterilized and otherwise prepared for storage, shipment and use. The medical needle shield apparatus may be manipulated by a handle and a removable sheath may be mounted therewith to enclose the components of the medical needle shield apparatus via friction, snap fit, interference fit, etc.

Referring to FIG. 1, the clinician (not shown) manipulates the medical needle shield apparatus such that shield 10 is in the retracted position and binding member 64 is in a non-binding or sliding orientation. Needle cannula 16 is fully extended relative to shield 10. A procedure employing the medical needle shield apparatus with stylet 34 is performed by the clinician to completion.

Needle cannula 16 is retracted proximally such that shield 10 is extended toward the extended position, as shown in FIG. 2. Binding member 64 is in the non-binding or sliding orientation such needle cannula 16 engages needle communicating surface 72 and binding surfaces 68 facilitate sliding through aperture 66, as discussed.

Referring to FIG. 3, as needle cannula 16 clears needle communicating surface 72, retainer 70 is free to rotate due to the canting forces created via the engagement of needle cannula 16 with frictional members 62. Aperture plate 65 rotates counter-clockwise, relative to longitudinal axis x, from the perpendicular orientation to an inclination for a binding orientation as facilitated by blocking members 40, 42. Aperture plate 65 rotates to angle a relative to longitudinal axis x.

In the binding orientation, binding surfaces 68 engage needle cannula 16 to bind and prevent axial movement of needle cannula 16 within housing 12 and lock the medical needle shield apparatus in a protective configuration. Shield 10 is disposed in the extended position to prevent hazardous exposure to distal end 14.

Figure 15:
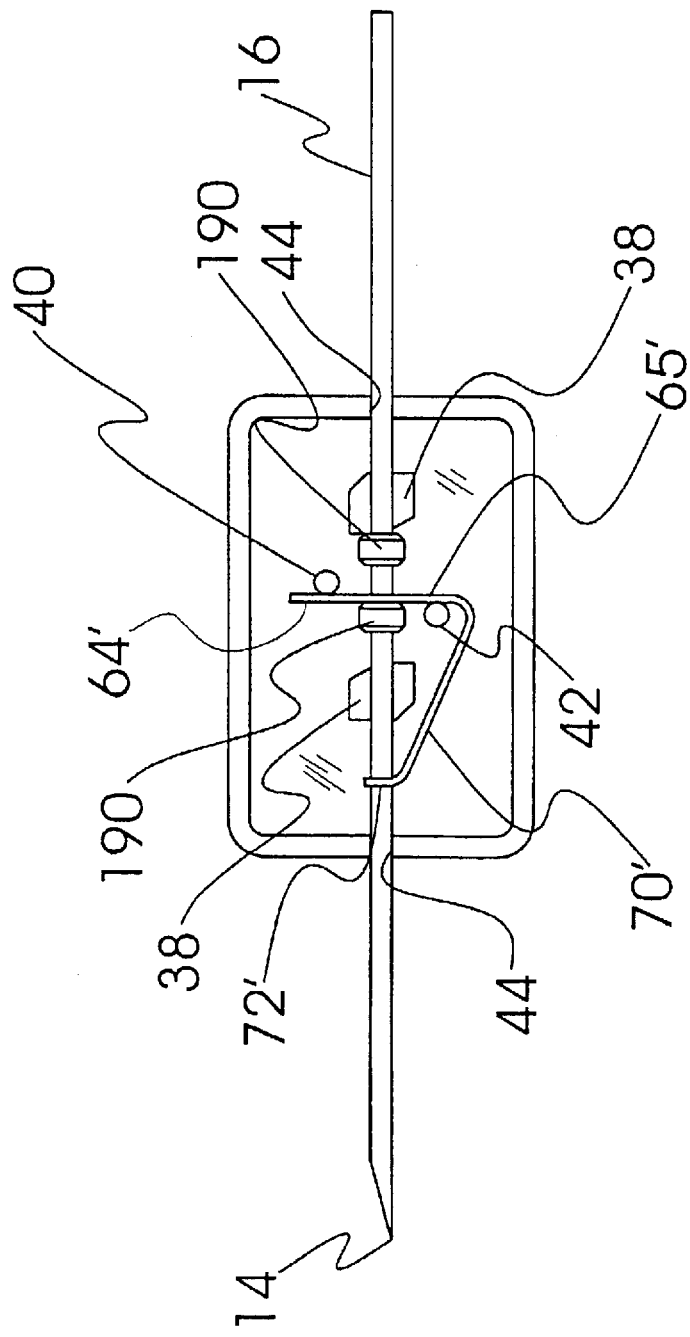
FIG. 15 is an enlarged perspective view of an alternate embodiment of the shield shown in FIG. 2, with a housing section removed.

In an alternate embodiment, as shown in FIG. 15, binding member 64' includes separate friction members 190 that are disposed on a proximal side and a distal side of aperture plate 65', respectively. Friction members 190 are friction fit polymer O-rings, which allow sliding of needle 16 therewith and provide a frictional drag force, similar to that discussed, via engagement with needle 16. The drag force is created as needle 16 slides and friction members 190 engage aperture plate 65'. Friction members 190 engage aperture plate 65', and in conjunction with blocking member 42, cause aperture plate 65' to move to the binding position. Binding surfaces 68 engage needle 16 to prevent axial movement of needle 16, as discussed. It is contemplated that friction members 190 may be fabricated from materials such as polymerics, metals, etc. It is also contemplated that the friction members 190 may have other shapes, including square, polygonal, ovoid etc.

Figure 16:
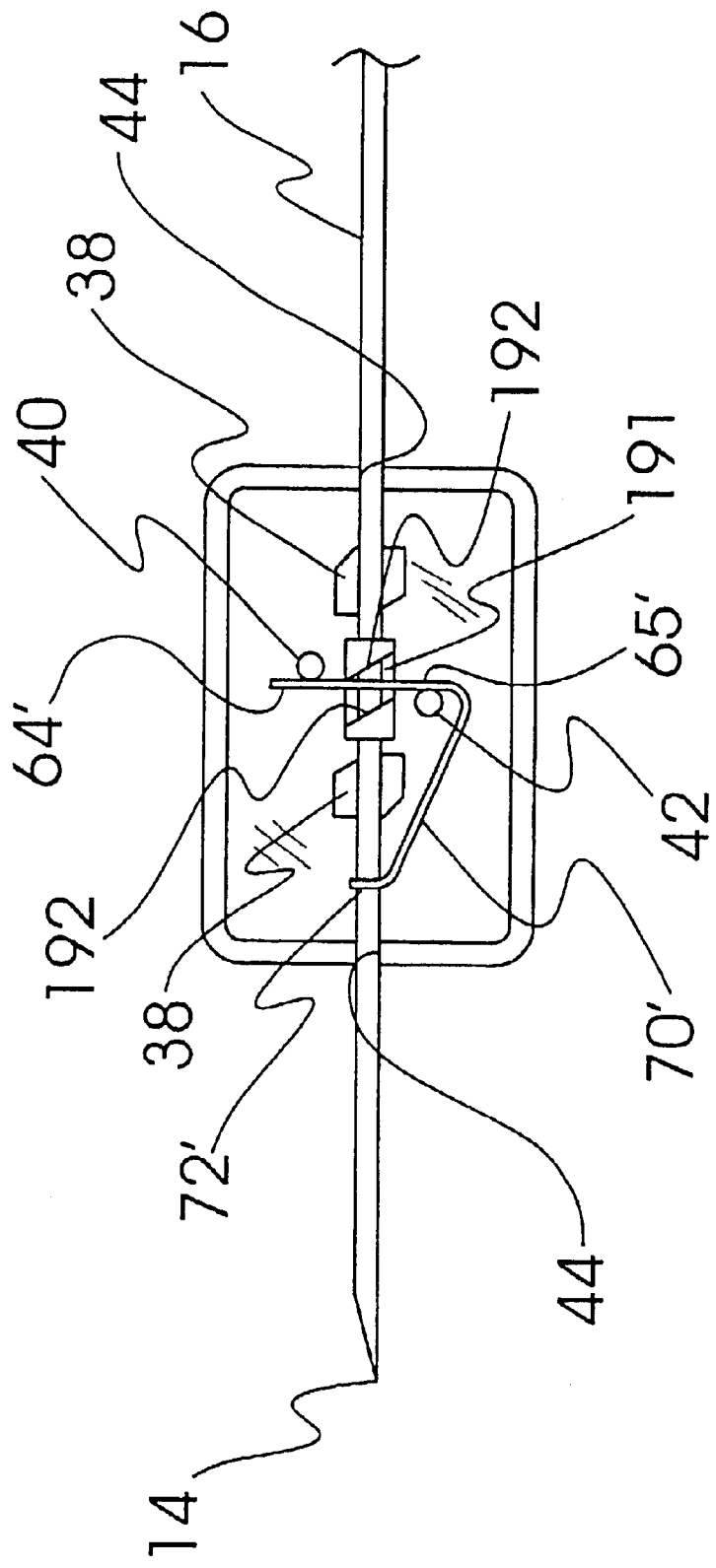
FIG. 16 is an enlarged perspective view of an alternate embodiment of the shield shown in FIG. 2, with a housing section removed.

Alternatively, friction members 190 may form a monolithic member 191 that links or joins two members 192, as shown in FIG. 16. Members 192 engage needle 16 and aperture plate 65' to prevent axial movement of needle 16, similar to that discussed with regard to FIG. 15. The drag force is created as needle 16 slides and friction members 192 engage aperture plate 65'. Friction members 192 engage aperture plate 65', and in conjunction with blocking member 42, cause aperture plate 65' to move to the binding position. Binding surfaces 68 engage needle 16 to prevent axial movement of needle 16, as discussed. It is further envisioned that materials such as, for example, jells, greases, etc. may be employed to create a frictional drag force with needle 16 to cause rotation of aperture plate 65'.

Figure 11:
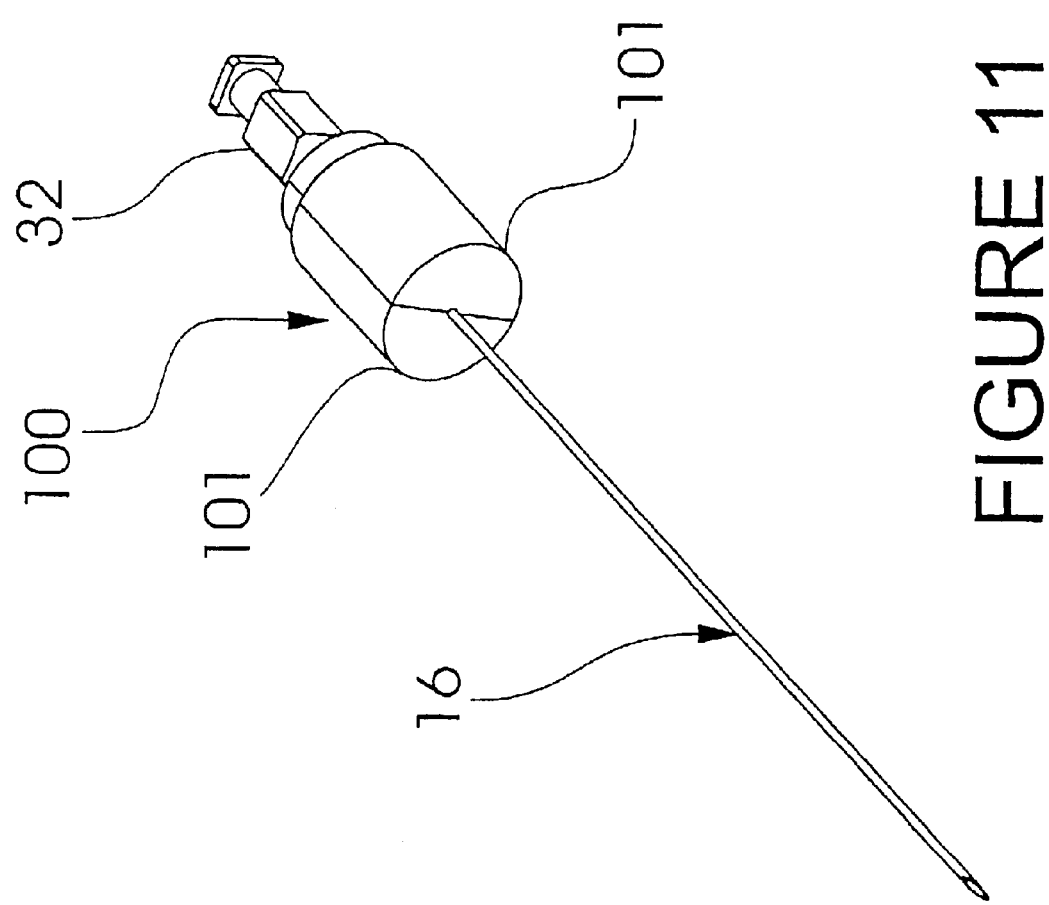
FIG. 11 is a perspective view of the medical needle shield apparatus shown in FIG. 9, in the retracted position.
Figure 12:
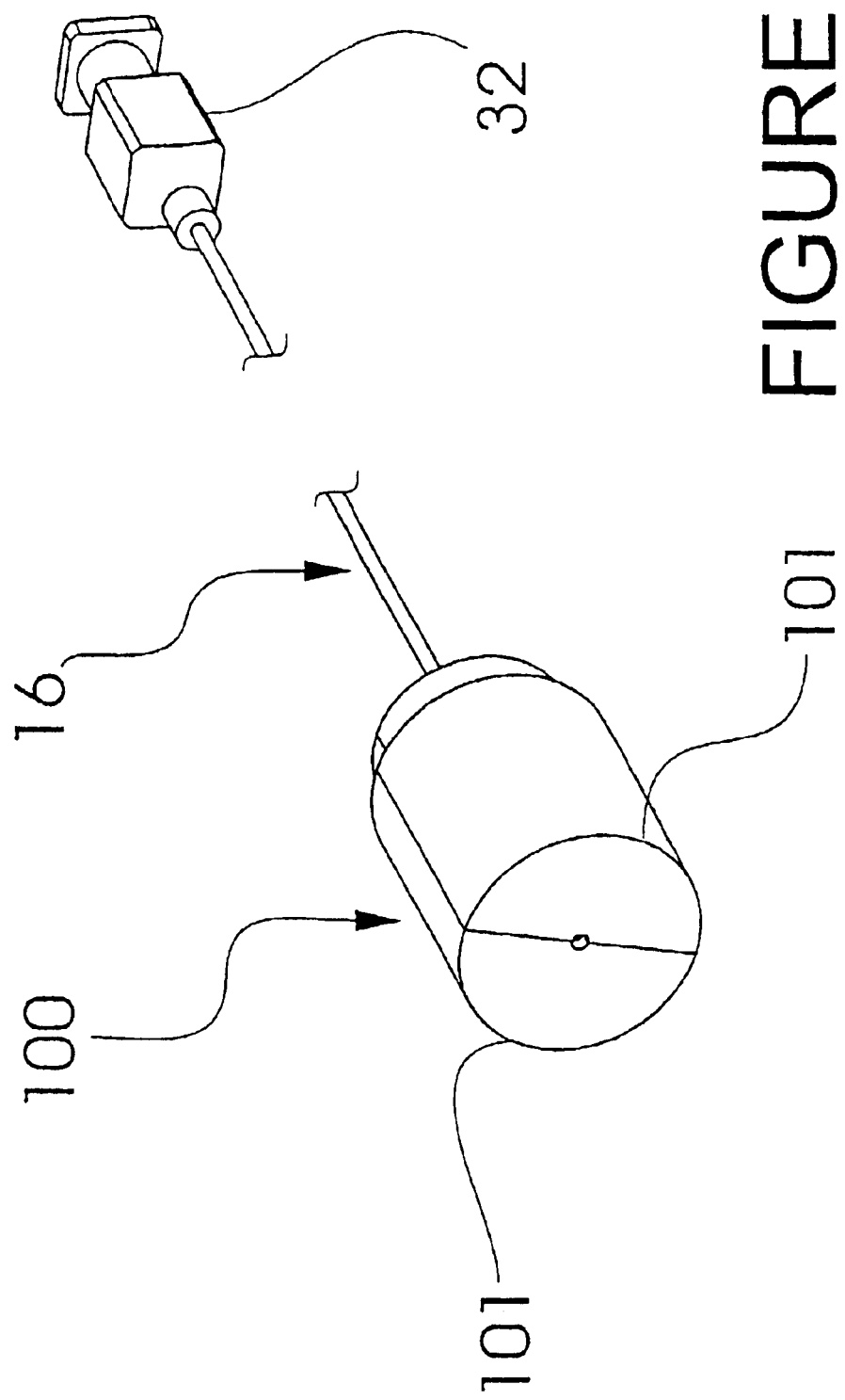
FIG. 12 is a perspective view of the medical needle shield apparatus shown in FIG. 9, in the extended position.

Referring to FIGS. 9–12, an alternate embodiment of the medical needle safety apparatus is shown. An outer rotatable housing 100, having sections 101, is disposed for rotation about and enclosure of shield 10 in the retracted position, as shown in FIG. 11. Outer rotatable housing 100 is mounted with shield 10, and freely rotates relative to shield 10 and needle cannula 16 in the extended position of shield 10, as shown in FIG. 12. Relative rotation of outer rotatable housing 100 is facilitated by support at opening 102 and opening 105 formed in outer rotatable housing 100. Openings 102, 105 support needle cannula 16 and facilitate free slidable rotation therein.

Outer rotatable housing 100 includes a bearing 103 that rotationally supports an axle 104 of housing 12, at corresponding distal ends thereof. This configuration advantageously limits radial engagement of shield 10 with outer rotatable housing 100. In a binding orientation, the bearing configuration and openings 102, 105 support rotation of outer rotatable housing 100 relative to shield 10 and needle cannula 16. Housing 12 includes blocking members 40, 42, similar to those discussed. It is envisioned that a bearing and axle similar to that comprised of 103 and 104 at the distal end of the shield may be formed at the proximal end of the shield.

Figure 13:
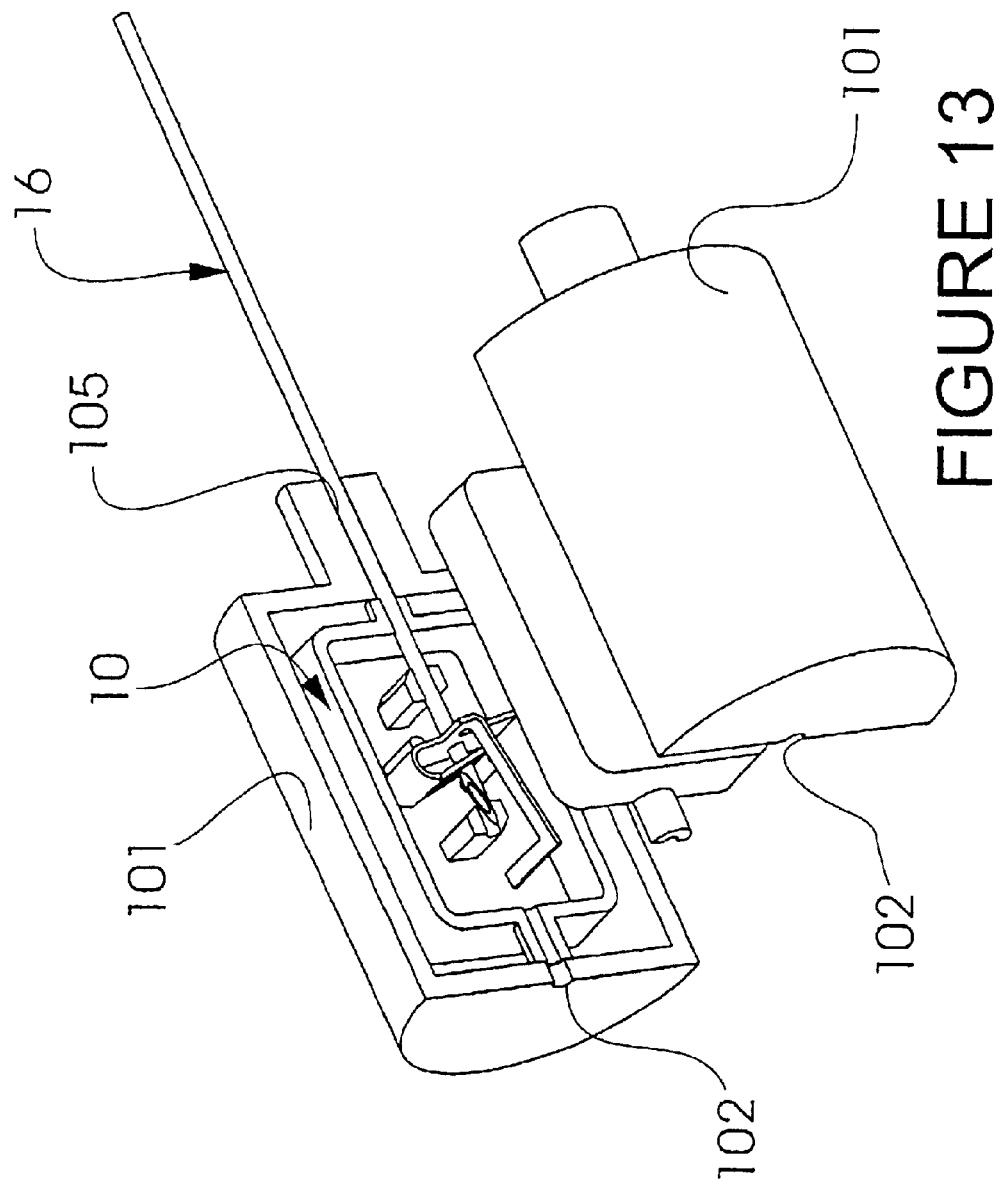
FIG. 13 is a cutaway perspective view of an alternate embodiment of the medical needle shield apparatus shown in FIG. 9 with parts separated.

This configuration prevents rotation of shield 10 about longitudinal axis x of needle cannula 16 such that binding member 64 is not undesirably rotated to disturb the protective binding engagement with needle cannula 16. Thus, the possibility of intentionally abusing and defeating the protective configuration of shield 10, in the extended position, by manually and abusively twisting shield 10 is reduced. In an alternate embodiment, as shown in FIG. 13, The bearing 103 and axle 104 may be deleted, and the length of opening 105 is increased such that the radial clearance of opening 105 with needle cannula 16 limits tilting of the needle 16, and thereby the shield 10 within outer rotatable housing 100. This configuration prevents radial contact of shield 10 with outer rotatable housing 100.

Figure 14:
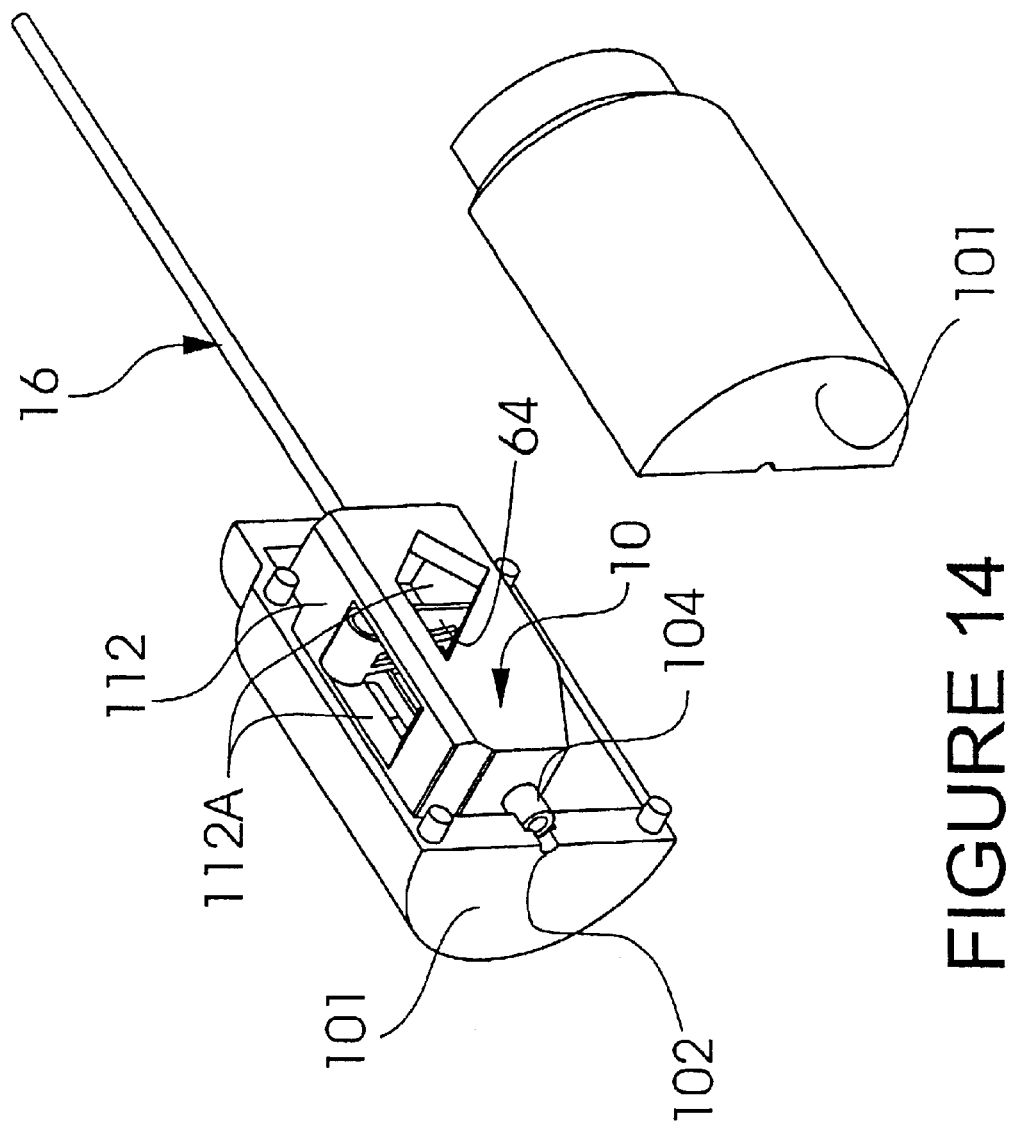
FIG. 14 is a cutaway perspective view of another alternate embodiment of the medical needle shield apparatus shown in FIG. 9 with parts separated.

Referring to FIG. 14, in another alternate embodiment, a housing 112 has a unitary body, eliminating the configuration employing separate housing sections. Housing 112 is mounted within outer rotatable housing 100 which is comprised of sections 101, and supports binding member 64 and needle cannula 16. It is envisioned that housing 112 may also incorporate blocking members 40, 42 and needle supports 38. It is further envisioned that housing 112 is monolithically formed. Housing 112 includes openings 112A for access to an interior thereof.

Figure 17:
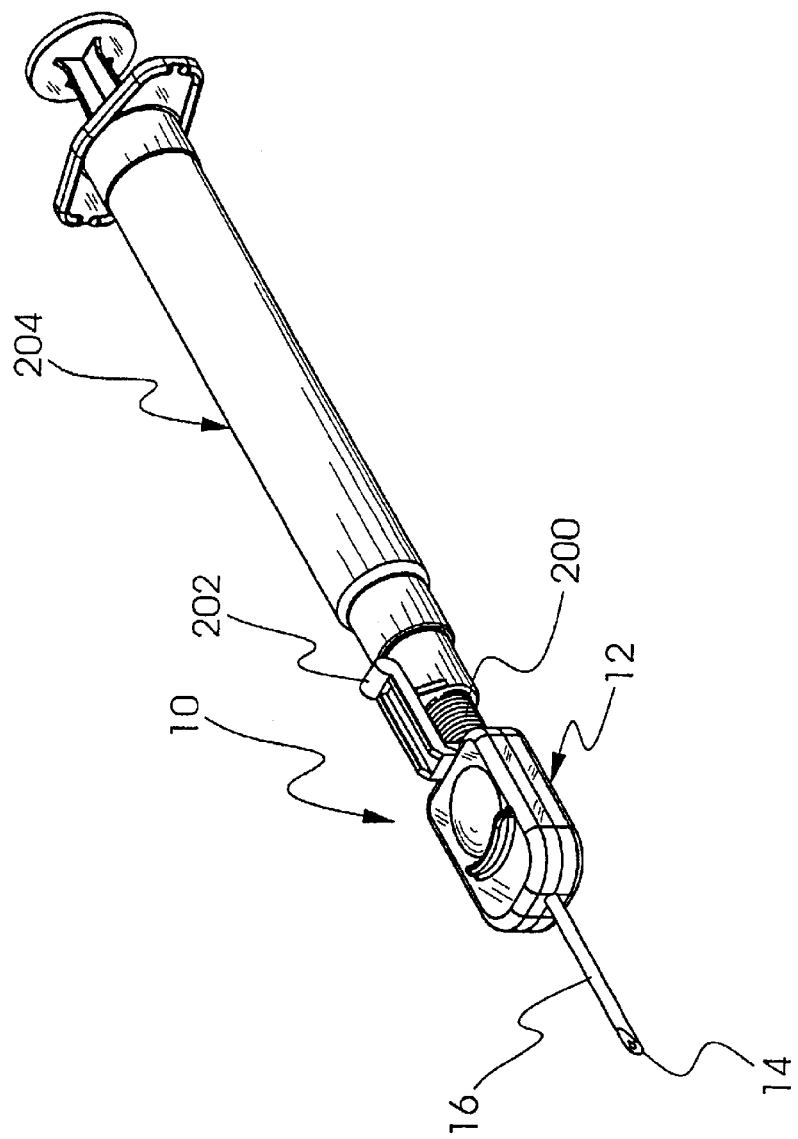
FIG. 17 is a perspective view of an alternate embodiment of the shield shown in FIG. 1 on a syringe in the pre-activation state.
Figure 18:
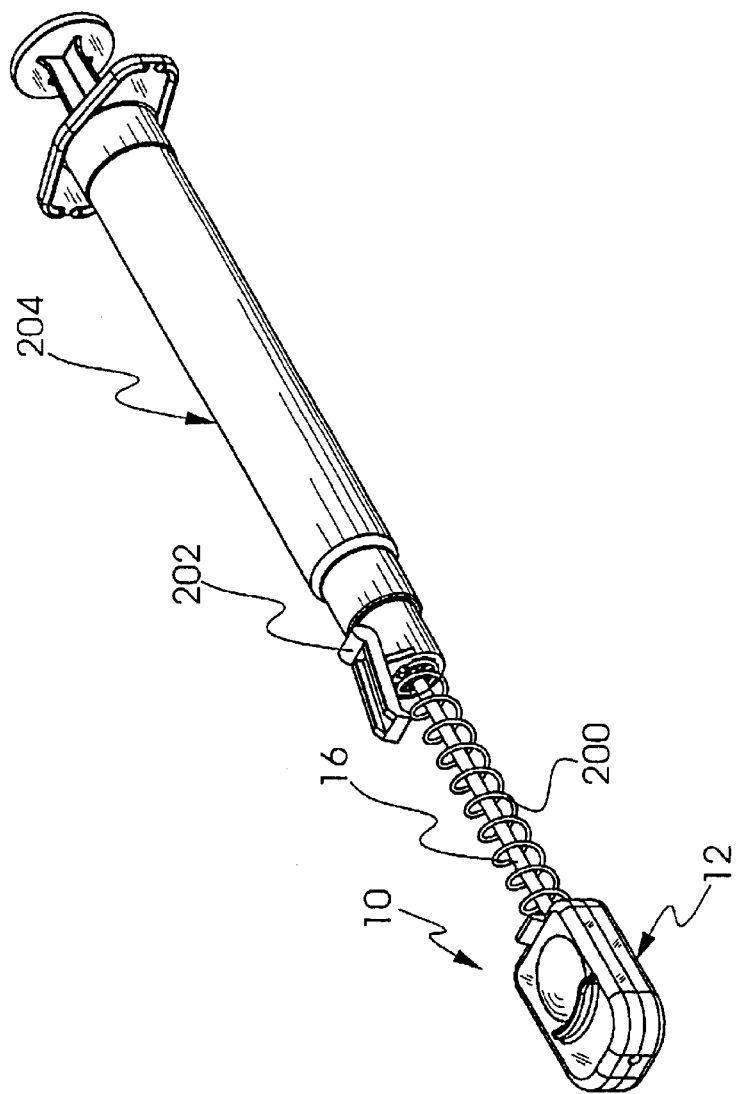
FIG. 18 is a perspective view of the embodiment shown in FIG. 17 in the post-activation state.

FIGS. 17 and 18 illustrate the safety shield assembly 10 disposed on a medical needle device 204, which includes a stored energy means, such as spring 200, for moving the shield 12 from a proximal position where the distal end 14 of the needle 16 is exposed to a distal position where the shield 12 covers the distal end 14 of the needle 16. The spring 200 is held in a biased and compressed state by means of a retainer 202, which is movable to release the spring 200 from a compressed state (shown in FIG. 17) to an extended state (shown in FIG. 18). It is envisioned that alternative methods may be employed to advance the shield. These methods include, but are not limited to, push rods, push or pull cables, push tapes (e.g., similar to the common tape measure), etc.

It is envisioned that the outer rotating housing may be comprised of a multiple of sections of various configurations, or may be monolithically formed, as is appropriate to the particular application.

The various shields disclosed above may be used to measure a desired insertion depth by positioning the shield along the needle at a desired insertion depth. It is also contemplated that the various shields disclosed above may be used to stabilize the needle by grasping the shield during insertion.

The invention of the present disclosure may be embodied in other specific forms without departing from the spirit or essential characteristics thereof. The present embodiments are therefore to be considered in all respects as illustrative and not restrictive; the scope of the invention being indicated by the appended claims rather than by the foregoing description, and all changes which come within the meaning and range of equivalency of the claims are therefore intended to be embraced therein.

What is claimed is:

1. A medical needle shield apparatus comprising:
   a shield being extensible from a retracted position to an extended position to enclose a distal end of a needle; and
   a binding member disposed within the shield and comprising binding surfaces that define an aperture configured for slidable receipt of the needle between the retracted position and the extended position,
   the binding member comprising a retainer extending therefrom such that the retainer is engageable with the needle to prevent inclination of the binding member while the retainer is engaged with the needle,
   the binding member further comprising at least one drag inducing member configured to engage the needle and create a drag force with the needle to cause inclination of the binding member relative to a longitudinal axis of the needle once the retainer extends beyond the distal end of the needle such that the binding surfaces engage the needle to prevent slidable movement of the needle in the extended position of the shield.

2. A medical needle shield apparatus as recited in claim 1, wherein the binding member comprises a substantially planar aperture plate that includes the binding surfaces that define the aperture.

3. A medical needle shield apparatus as recited in claim 2, wherein the aperture plate is substantially perpendicular relative to the longitudinal axis of the needle due to engagement of the retainer with the needle when not in the extended position.

4. A medical needle shield apparatus as recited in claim 1, wherein the retainer comprises a first portion extending from the binding member and a second portion extending from the first portion.

5. A medical needle shield apparatus as recited in claim 4, wherein the first portion extends from the binding member in substantially parallel alignment with the needle due to engagement of the retainer with the needle.

6. A medical needle shield apparatus as recited in claim 4, wherein the second portion extends transversely relative to the longitudinal axis of the needle and is configured for engagement with the needle.

7. A medical needle shield apparatus as recited in claim 6, wherein the second portion has a substantially planar portion for engagement with the needle.

8. A medical needle shield apparatus as recited in claim 7, wherein the substantially planar portion of the second portion defines a retainer cavity.

9. A medical needle shield apparatus as recited in claim 1, wherein the at least one drag inducing member comprises the aperture of the binding member such that the aperture engages the needle to create the drag force with the needle.

10. A medical needle shield apparatus as recited in claim 1, wherein the at least one drag inducing member comprises a pair of friction members that extend to engage the needle to create the drag force with the needle.

11. A medical needle shield apparatus as recited in claim 10, wherein the pair of friction members defines a cavity that is substantially aligned with the aperture, the cavity being configured for slidable receipt of the needle to create the drag force with the needle.

12. A medical needle shield apparatus as recited in claim 1, wherein the at least one drag inducing member comprises at least one friction member disposed on the needle.

13. A medical needle shield apparatus as recited in claim 1, wherein the at least one drag inducing member is integral to the binding member.

14. A medical needle shield apparatus as recited in claim 1, wherein the at least one drag inducing member comprises a unitary friction element disposed on the medical needle.

15. A medical needle shield apparatus as recited in claim 14, wherein the unitary friction element comprises friction elements for canting the binding member and the aperture of the binding member is disposed between the friction elements.

16. A medical needle shield apparatus as recited in claim 1, wherein the retainer includes a slot to release a guidewire.

17. A medical needle shield apparatus as recited in claim 1, wherein the binding member is rotatable, relative to the longitudinal axis of the needle, between a non-binding orientation whereby the needle is slidable relative to the binding member and a binding orientation whereby the binding surfaces engage the needle to prevent slidable movement of the needle in the extended position of the shield.

18. A medical needle shield apparatus as recited in claim 17, wherein the shield comprises a housing that defines at least one blocking member extending from an interior surface thereof, the at least one blocking member being engageable with the binding member for urging the binding member to the binding orientation.

19. A medical needle shield apparatus as recited in claim 1, further comprising an outer rotatable housing that encloses the shield, the outer rotatable housing supporting the shield for relative rotational movement therewith.

20. A medical needle shield apparatus as recited in claim 19, wherein the shield is supported for relative rotational movement by the outer rotatable housing by at least one bearing.

21. A medical needle shield apparatus as recited in claim 1, wherein the shield is positioned to indicate needle insertion depth.

22. A medical needle shield apparatus as recited in claim 1, further comprising a means for extending the shield to the distal end of the needle.

23. A medical needle shield apparatus comprising:
  a shield being extensible from a retracted position to an extended position to enclose a distal end of a needle; and
  a binding member disposed within the shield and comprising an aperture for slidable receipt of the needle between the retracted position and the extended position,
  the binding member comprising retainer means for inclination of the binding member while the retainer means is engaged with the needle.
  the binding member further comprising drag inducing means for inclining the binding member relative to a longitudinal axis of the needle by generating frictional drag forces with the needle once the retainer extends beyond the distal end of the needle, and a binding surface means for engaging the needle to prevent slidable movement of the needle in the extended position of the shield.

24. A medical needle shield apparatus as recited in claim 23, wherein the binding member is rotatable, relative to the longitudinal axis of the needle, between a non-binding orientation whereby the needle is slidable relative to the binding member and a binding orientation whereby the binding surface means engages the needle to prevent slidable movement of the needle in the extended position of the shield.

25. A medical needle shield apparatus as recited in claim 23, further comprising an outer rotatable housing that encloses the shield, the outer rotatable housing supporting the shield for relative rotational movement therewith in the extended position of the shield.

26. A medical needle shield apparatus as recited in claim 25, wherein the shield is supported for relative rotational movement by the outer rotatable housing by at least one bearing.

27. A medical needle shield apparatus as recited in claim 23, wherein the at least one drag inducing member comprises at least one friction member disposed on the needle.

28. A medical needle shield apparatus as recited in claim 23, wherein the at least one drag inducing member is integral to the binding member.

29. A medical needle shield apparatus as recited in claim 23, wherein the at least one drag inducing member comprises a unitary friction element disposed on the medical needle.

30. A medical needle shield apparatus as recited in claim 29, wherein the unitary friction element comprises friction elements for canting the binding member and the aperture of the binding member is disposed between the friction elements.

31. A medical needle shield apparatus as recited in claim 23, wherein the retainer includes a slot to release a guidewire.

32. A medical needle shield apparatus as recited in claim 23, further comprising a means for extending the shield to the distal end of the needle.

33. A medical needle shield apparatus comprising:
  a shield being extensible from a retracted position to an extended position to enclose a distal end of a needle;
  a binding member disposed within the shield and comprising binding surfaces that define an aperture configured for slidable receipt of the needle between the retracted position and the extended position,
  the binding member being inclinable, relative to a longitudinal axis of the needle, between a non-binding orientation whereby the needle is slidable relative to the binding member and a binding orientation whereby the binding surfaces engage the needle to prevent slidable movement of the needle in the extended position of the shield,
  the binding member comprising a retainer extending therefrom, the retainer comprising a first portion extending from the binding member and a second portion extending from the first portion, such that the second portion is engageable with the needle to prevent inclination of the binding member while the retainer is engaged with the needle,
  the binding member further comprising a pair of drag inducing members that extend to define a cavity that is substantially aligned with the aperture, the cavity being configured for slidable receipt of the needle between the retracted position and the extended position, the drag inducing members being configured to engage and create a drag force with the needle to cause rotation of the binding member relative to the longitudinal axis of the needle to the binding orientation once the retainer extends beyond the distal end of the needle, and
  an outer rotatable housing that encloses the shield, the outer rotatable housing supporting the shield for relative rotational movement therewith in the extended position of the shield, the shield being supported for relative rotational movement by the outer rotatable housing by at least one bearing.

* * * * *